US012781247B2

(12) United States Patent
Foody

(10) Patent No.: US 12,781,247 B2
(45) Date of Patent: Nov. 3, 2026

(54) CONVERTING CELLULOSIC BIOMASS TO FUEL

(71) Applicant: Iogen Corporation, Ottawa (CA)

(72) Inventor: Brian Foody, Ottawa (CA)

(73) Assignee: Iogen Corporation, Ottawa (CA)

( * ) Notice: Subject to any disclaimer, the term of this patent is extended or adjusted under 35 U.S.C. 154(b) by 279 days.

(21) Appl. No.: 18/564,363

(22) PCT Filed: May 19, 2022

(86) PCT No.: PCT/CA2022/050794

§ 371 (c)(1),
(2) Date: Nov. 27, 2023

(87) PCT Pub. No.: WO2022/246546

PCT Pub. Date: Dec. 1, 2022

(65) Prior Publication Data

US 2024/0263197 A1 Aug. 8, 2024

Related U.S. Application Data

(60) Provisional application No. 63/202,159, filed on May 28, 2021.

(51) Int. Cl.
*C12P 5/02* (2006.01)
*C10L 3/10* (2006.01)
*C12P 3/00* (2006.01)

(52) U.S. Cl.
CPC ........... *C12P 5/023* (2013.01); *C12P 2203/00* (2013.01)

(58) Field of Classification Search
CPC ......... C12P 5/023; C12P 2203/00; C12P 3/00; C12P 7/64; C10G 1/065; C10L 3/104; Y02E 50/30
See application file for complete search history.

(56) References Cited

U.S. PATENT DOCUMENTS

| | | | |
|---|---|---|---|
| 7,198,925 | B2 | 4/2007 | Foody |
| 8,658,026 | B2 | 2/2014 | Foody et al. |
| 8,753,854 | B2 | 6/2014 | Foody |
| 8,945,373 | B2 | 2/2015 | Foody |
| 9,040,271 | B2 | 5/2015 | Foody |
| 9,217,162 | B2 | 12/2015 | Chen et al. |
| 9,376,697 | B2 | 6/2016 | Nokes et al. |
| 9,404,063 | B2 | 8/2016 | Elliott et al. |
| 9,816,035 | B2 | 11/2017 | Lehoux et al. |
| 9,963,665 | B2 | 5/2018 | Feldmann |
| 10,093,540 | B2 | 10/2018 | Foody |
| 10,421,663 | B2 | 9/2019 | Foody |
| 10,428,353 | B2 | 10/2019 | Foody |
| 10,513,714 | B2 | 12/2019 | Foody et al. |
| 10,689,282 | B2 | 6/2020 | Xu et al. |
| 10,723,621 | B2 | 7/2020 | Foody |
| 10,907,303 | B2 | 2/2021 | Toll et al. |
| 10,981,784 | B2 | 4/2021 | Foody |
| 11,168,339 | B1 | 11/2021 | Stepany et al. |
| 11,193,144 | B2 | 12/2021 | Foody |
| 11,198,764 | B2 | 12/2021 | Kleinhout et al. |
| 11,352,596 | B2 | 6/2022 | Ludtke et al. |
| 11,827,916 | B2 | 11/2023 | Foody et al. |
| 2002/0102673 | A1 | 8/2002 | Zhang et al. |
| 2013/0319261 | A1 | 12/2013 | Kelly et al. |
| 2014/0308727 | A1 | 10/2014 | Castelli |
| 2015/0118723 | A1 | 4/2015 | Duzoglou |
| 2021/0285017 | A1 | 9/2021 | Feldmann et al. |
| 2023/0340543 | A1 | 10/2023 | Foody et al. |

FOREIGN PATENT DOCUMENTS

| | | | |
|---|---|---|---|
| CN | 103740767 | A | 4/2014 |
| CN | 107473549 | A | 12/2017 |
| EP | 2 160 458 | B1 | 7/2018 |
| EP | 3450405 | A1 | 3/2019 |
| GB | 2 625 949 | A | 7/2024 |
| WO | WO 2005/054423 | A3 | 6/2005 |
| WO | WO 2011/101137 | A1 | 8/2011 |
| WO | WO 2015/003273 | A1 | 1/2015 |
| WO | WO 2021/258165 | A1 | 12/2021 |

(Continued)

OTHER PUBLICATIONS

Tanigawa S . . . , "BIOGAS: Converting Waste to Energy", Environmental and Energy Study Institute (EESI at the web—www.eesi.org), Oct. 2017, Total pp. 1-6. (Year: 2017).*
Xia Z., CN 107473549 A—English machine translation, "An Agricultural Waste Recycling System", Pub. Dec. 15, 2017, total pp. 1-7. (Year: 2017).*
International Preliminary Report on Patentability issued Nov. 21, 2023 for PCT Application No. PCT/CA2022/050794.
Gao, J. et al., "Mass conversion pathway during anaerobic digestion of wheat straw", RSC Advances, 2020, vol. 10, pp. 27720-27727.
Jain, S. et al., "Global Potential of Biogas", World Biogas Association, WBA Global Report, Jun. 2019, in 56 pages.
Kovacic, D. et al., "Digestate Management and Processing Practices: A Review", Applied Sciences, Sep. 2022, vol. 12, in 35 pages.
Kratzeisen, M. et al., "Applicability of biogas digestate as solid fuel", Fuel, Feb. 2010, vol. 89, pp. 2544-2548.

(Continued)

*Primary Examiner* — Satyendra K Singh
(74) *Attorney, Agent, or Firm* — Knobbe, Martens, Olson & Bear, LLP

(57) ABSTRACT

A process for converting cellulosic biomass to fuel includes loading bales of cellulosic biomass into an enclosure, at least partially filling the enclosure with an aqueous liquid, wherein the aqueous liquid is filled to a level selected to at least partially submerge the bales of cellulosic biomass once loaded into the enclosure, and subjecting the bales loaded within the enclosure to an anaerobic digestion to produce biogas. The biogas, which contains methane, is provided as a fuel, is upgraded to provide a fuel. The biogas or upgraded biogas can be used to produce a fuel, chemical, or product. A process for converting biomass to fuel includes subjecting cellulosic biomass to anaerobic digestion, and feeding at least a portion of the digestate to hydrothermal liquefaction to produce bio-oil.

18 Claims, 4 Drawing Sheets

(56) References Cited

FOREIGN PATENT DOCUMENTS

| | | |
|---|---|---|
| WO | WO 2022/246546 | 12/2022 |
| WO | WO 2023/092138 A1 | 5/2023 |
| WO | WO 2023/208306 | 11/2023 |

OTHER PUBLICATIONS

Lisowyj, M. et al., "A review of biogas and an assessment of its economic impact and future role as a renewable energy source", Review of Chemical Engineering, Sep. 2020, vol. 36(3), pp. 401-421.
Nsair, A. et al., "Operational Parameters of Biogas Plants: A Review and Evaluation Study", Energies, Jul. 2020, vol. 13, 3761, in 27 pages.
Sawyerr, N. et al., "An Overview of Biogas Production: Fundamentals, Applications and Future Research", International Journal of Energy Economics and Policy, 2019, vol. 9(2), pp. 105-116.
Sayara, T. et al., "A Review on Anaerobic Digestion of Lignocellulosic Wastes: Pretreatments and Operational Conditions", Applied Sciences, Nov. 2019, vol. 9, 4655, in 23 pages.
Singlitico, A. et al., "Can thermal energy recovery from digestate make renewable gas from household waste more cost effective? A case study for the Republic of Ireland", Journal of Cleaner Production, Mar. 2020, vol. 261, Dec. 11, 1998, in 13 pages.
Singlitico, A. et al., "Techno-economic Optimisation of Combined Anaerobic Digestion and Gasification of Food Waste as part of an Integrated Waste Management and Energy System", 25th European Biomass Conference and Exhibition, Jun. 2017, pp. 96-105.
Skinner, C. et al., "Pressurised disc refining of wheat straw as a pre-treatment approach for agricultural residues: A preliminary assessment of energy consumption and fibre composition", Bioresource Technology, Feb. 2020, vol. 304, Dec. 29, 1976, in 7 pages.
Wu, D. et al., "Commercial biogas plants: Review on operational parameters and guide for performance optimization", Fuel, Jun. 2021, vol. 303, Dec. 12, 1982, in 14 pages.
Al Naami, Adam; "Techno-economic Feasibility Study of a Biogas Plant for Treating Food Waste Collected from Households in Kartamantul Region, Yogyakarta" KTH Industrial Engineering and Management, Master of Science Thesis (2017).
Bioenergy International—Digital Biogas Special Jan. 2020, pp. 8-12.
Fu et al., "Dry Anaerobic Digestion Technologies for Agricultural Straw and Acceptability in China", Sustainability (2018) 10, 4588.
Gummert et al., "Sustainable Rice Straw Management", e-book, Springer Open, 2020.
Hoffmann et al., "Conceptual Design of an Integrated Hydrothermal Liquefaction and Biogas Plant for Sustainable Bioenergy Production", Bioresource Technology (2013) 129, 402-410.
Madsen et al., "How do Hydrothermal Liquefaction Conditions and Feedstock Type Influence Product Distribution and Elemental Composition?", Ind. Eng. Res. (2019) 58, 17583-17600.
Marashi Shoushtari, Nafees Sadat, "Partial Upgrading of Lignocellulosic Bio-Oil via Deep Catalytic Hydrotreating," University of Calgary, Master Thesis (2021).
Montgomery et al., "Pretreatment of Feedstock for Enhanced Biogas Production", Technical Brochure, IEA Bioenergy, (2014).
Murphy et al., "Biogas from Crop Digestion", Task 37—Energy from Biogas, IEA Bioenergy, (2011).
Nicholson et al., "Straw Incorporation Review", Research Review No. 81, Agriculture and Horticulture Development Board (HGCA) (2014).
Panwar et al., "An Overview of Recent Development in Bio-Oil Upgrading and Separation Techniques", Environ. Eng. Res. (2021) 26, 200382.
Reza et al., "Evaluation of Integrated Anaerobic Digestion and Hydrothermal Carbonization for Bioenergy Production", J. Vis. Exp. (2014) 88, e51734.
Written Opinion and International Search Report of PCT/CA2022/050794 dated Aug. 23, 2022.
Drosg et al., "Nutrient Recovery by Biogas Digestate Processing", IEA Bioenergy Technical, 2015, in 40 pages (brochure).

* cited by examiner

CONVERTING CELLULOSIC BIOMASS TO FUEL

TECHNICAL FIELD

The present disclosure relates generally to a process and/or system whereby cellulosic biomass is treated by anaerobic digestion to produce biogas, and more specifically, where bales of cellulosic biomass are treated by anaerobic digestion to produce fuel, chemical(s), and/or product(s) and/or where digestate from the anaerobic digestion of cellulosic biomass is treated by hydrothermal liquefaction.

BACKGROUND

Cellulosic biomass, such as straw, is a promising renewable resource for the production of fuels and chemicals. Straw, which can refer to the stalks of cereal crops such as wheat, oat, barley, rye, and rice, remaining after the grain and/or chaff (e.g., seed heads) have been removed, is an abundant agricultural waste product. Once gathered, straw is often stored in bales for eventual use as animal bedding or as a roughage component of the diet of cattle or horses. Straw not used as bedding or fodder may be viewed as surplus and may be ploughed back into the ground. Using straw as a feedstock for a process that converts cellulosic biomass to fuel (e.g., gaseous, liquid, or solid) can harness the energy content within this agricultural residue.

Anaerobic digestion is one option for producing fuel or chemicals from straw. Anaerobic digestion, which refers to refers to the biological breakdown of organic matter by microorganisms under anaerobic or low oxygen conditions, can produce biogas. Biogas, which is a mixture of gases primarily composed of methane ($CH_4$) and carbon dioxide ($CO_2$), can be used directly as a fuel (e.g., to generate heat and/or power) or can be upgraded to produce gas that is primarily $CH_4$ (e.g., >95% $CH_4$). If of sufficient purity, upgraded biogas may be used interchangeably with natural gas and may be referred to as renewable natural gas (RNG). Upgraded biogas, such as RNG, can be used as a fuel and/or used to produce fuel or chemicals.

The production of biogas from the anaerobic digestion of cellulosic biomass, such as straw, is typically conducted in an anaerobic digester. Anaerobic digesters, which are generally engineered to facilitate the breakdown of organic material by microorganisms under anaerobic or low oxygen conditions, can be configured to operate using a number of different configurations including, but not limited to, batch versus continuous, mesophilic versus thermophilic, dry versus wet, and/or single stage versus multistage.

Dry anaerobic digesters are designed to treat solid substrates without the addition water, or with the addition of only a small amount of water (e.g., are operated with a total solids content greater than 15-20%), such that little free water is present. For example, dry anaerobic digesters can be continuous vertical plug flow digesters, continuous horizontal plug flow digesters, or garage-type digesters. Continuous vertical plug flow dry digesters are often upright, cylindrical tanks where feedstock is continuously fed into the top of the digester, flows downward by gravity during digestion, and is removed from the bottom as digestate. As a result of the high solids content, there typically is no stirring in dry anaerobic digestions although some continuous horizontal plug flow dry digesters may have a mechanism (e.g., transversely orientated agitators or slowly rotating impellers) used to move the biomass through the digester. In a garage-type digester, which is operated in batch mode, the feedstock can be stacked in the digester, which often includes an airtight door. Such reactors often operate at the higher end of the total solids content (e.g., greater than 30%). In some dry anaerobic systems, liquid is recirculated over the feedstock (e.g., percolate collected from the bottom of the reactor can be sprayed over the top of the feedstock).

Wet anaerobic digesters are often designed to process slurries, and more specifically, are often designed to process slurries that can be pumped, heated, and stirred (e.g., having a consistency less than <15-20%). Wet digestion is often viewed as preferable to dry digestion as it may be operated as a continuous process (e.g., which may be more economical than batch) and/or may be associated with higher biogas production over a shorter time period. For example, the addition of water and/or stirring may allow the anaerobic microorganisms to access more substrate, provides more efficient heat transfer, and/or more efficient nutrient transfer.

While the anaerobic digestion of straw, and in particular, the wet anaerobic digestion of straw is promising in terms of biogas production, straw is not generally viewed as an ideal substrate for wet anaerobic digestion. Straw is often very dry (e.g., >85% total solids (TS)) and is slow to absorb water due to its waxy exterior. Straw is a fibrous material that has a very low bulk density (e.g., a loose bulk density of <50 $kg/m^3$) and tends to get caught in the mixing equipment (e.g., paddle wheels or propellers). While straw may be subjected to size reduction (e.g., chopping), this can create physical problems like floating, foaming, and/or clumping. To prevent these physical problems associated with chopped fibers and/or to prevent the chopped fibers or clumps of chopped fibers from blocking pumps, pipes, or the mixing equipment, appropriate homogenization and/or stirring is typically required. For example, in addition to maximizing contact of the microorganisms with the substrate, thereby accelerating the digestion process, stirring can minimize solids deposition at the bottom of the digesters and/or avoid foaming and scum at the surface of the digester contents. However, as a light, dry material, chopped straw can increase the solids content in the digester, which can require specialized mixing equipment and/or is often associated with high power requirements. This can be challenging when the anaerobic digestion is conducted in a vessel containing several million gallons of slurry.

In addition, cellulosic substrates such as straw can be difficult to digest (e.g., lignin can slow microbial access to cellulose and hemicellulose). As a result, it is generally understood that straw substrates should be pretreated upstream of anaerobic digestion in order to speed up the anaerobic digestion and/or maximize biogas production. For example, such pretreatment can include physical, chemical, and/or biological pretreatment. Physical pretreatment can reduce the size of feedstock particles (e.g., chopping, grinding, etc.), which can affect biogas production (e.g., smaller particles have larger surface areas and increased microbial activity, resulting in faster decomposition). Chemical treatment (e.g., weak acid hydrolysis) and/or biological treatment (e.g., microaerobic treatments, ensiling or composting, and fungi pretreatments) can make the substrate more amenable to digestion.

SUMMARY

The present disclosure describes certain embodiments wherein bales of cellulosic biomass, such as straw, are treated by anaerobic digestion in a process that includes adding aqueous liquid (e.g., water) to the bales of cellulosic biomass (e.g., to provide the anaerobic digester with a solids content less than 15%). Since the cellulosic biomass is baled for at least an initial part of the anaerobic digestion, challenges associated with mixing loose fiber particles may be reduced. In addition, since bales of cellulosic biomass are provided for the anaerobic digestion (e.g., as obtained from the field), there can be reduced cost associated with feedstock preparation and/or storage. For example, as the process typically does not require unbaling, grinding, size reduction, and/or slurry transfer, upstream of the anaerobic digestion, there can be reduced capital and/or operating costs.

The present disclosure also describes certain embodiments wherein cellulosic biomass, such as straw (e.g., milled or baled), is treated by anaerobic digestion and at least part of the digestate produced from the anaerobic digestion is treated by hydrothermal liquefaction to produce bio-oil and/or char. The bio-oil can be used as a fuel, or processed to produce a fuel, or the bio-oil and/or char can be part of a carbon capture and storage process to reduce lifecycle greenhouse gas emissions of the biogas, or a fuel, chemical, or product, produced from the biogas.

In accordance with one aspect of the instant invention there is provided a process for converting cellulosic biomass to fuel, the process comprising: loading bales of cellulosic biomass into an enclosure; at least partially filling the enclosure with an aqueous liquid, wherein the aqueous liquid is filled to a level selected to at least partially submerge the bales of cellulosic biomass once loaded into the enclosure; providing anaerobic conditions within the enclosure; subjecting the bales loaded within the enclosure to an anaerobic digestion to produce biogas, the biogas comprising methane, the anaerobic digestion producing digestate; and, collecting at least a portion of the biogas produced from the anaerobic digestion of the bales of cellulosic biomass.

In accordance with one aspect of the instant invention there is provided a process for converting cellulosic biomass to fuel, the process comprising: loading straw bales into an enclosure, the loading comprising stacking the straw bales, each of the straw bales having a density between 80 to 250 $kg/m^3$; adding aqueous liquid to the enclosure such that the straw bales within the enclosure are in contact with the aqueous liquid, the aqueous liquid added to a level such that substantially all non-floating straw bales are submerged; introducing inoculum into at least one of the straw bales, the aqueous liquid, or the enclosure; sealing the enclosure; subjecting the bales within the sealed enclosure to an anaerobic digestion to produce biogas, the anaerobic digestion conducted for at least 25 days; and, collecting at least a portion of the biogas produced from the anaerobic digestion of the straw bales.

In accordance with one aspect of the instant invention there is provided a process for converting cellulosic biomass to fuel, the process comprising: loading bales of cellulosic biomass into an enclosure; at least partially filling the enclosure with an aqueous liquid, wherein the aqueous liquid is filled to a level selected to at least partially submerge the bales of cellulosic biomass once loaded into the enclosure; providing anaerobic conditions within the enclosure; subjecting the bales loaded within the enclosure to an anaerobic digestion to produce biogas, the biogas comprising methane, the anaerobic digestion producing digestate; collecting at least a portion of the biogas produced from the anaerobic digestion of the bales of cellulosic biomass; and producing the fuel from the digestate, said producing comprising subjecting at least a portion of a solid fraction of the digestate to a hydrothermal liquefaction, thereby producing bio-oil, wherein the fuel comprises the bio-oil or is derived from the bio-oil.

In accordance with one aspect of the instant invention there is provided a process for converting cellulosic biomass to fuel, the process comprising: subjecting the cellulosic biomass to an anaerobic digestion to produce biogas, the biogas comprising methane, the anaerobic digestion producing digestate; collecting at least a portion of the biogas produced from the anaerobic digestion of the cellulosic biomass; and producing fuel from the digestate, said producing comprising subjecting at least a portion of a solid fraction of the digestate to a hydrothermal liquefaction, thereby producing bio-oil, wherein the fuel comprises the bio-oil or is derived from the bio-oil.

In accordance with one aspect of the instant invention there is provided a process for converting straw to fuel, chemical, or product, the process comprising: receiving bales of straw from one or more sources; subjecting straw from the bales to an anaerobic digestion to produce biogas, the biogas comprising methane, the anaerobic digestion producing digestate; collecting at least a portion of the biogas produced from the anaerobic digestion of the straw; and subjecting at least a portion of the solids from the digestate to a hydrothermal liquefaction to produce bio-oil; providing fuel that comprises the bio-oil or is derived from the bio-oil.

DETAILED DESCRIPTION

Figure 1:
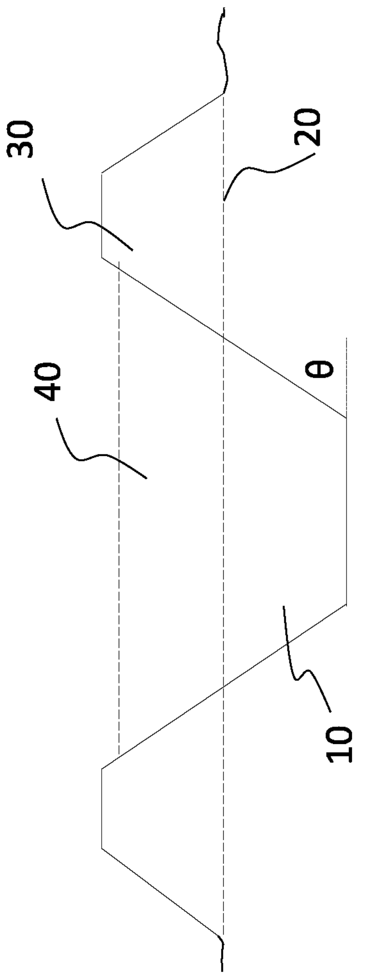
FIG. 1 is a schematic diagram of an earthen basin.

Certain exemplary embodiments of the invention now will be described in more detail, with reference to the drawings, in which like features are identified by like reference numerals. The invention may, however, be embodied in many different forms and should not be construed as limited to the embodiments set forth herein.

The terminology used herein is for the purpose of describing certain embodiments only and is not intended to be limiting of the invention. For example, as used herein, the singular forms "a," "an," and "the" may include plural references unless the context clearly dictates otherwise. The terms "comprises", "comprising", "including", and/or "includes", as used herein, are intended to mean "including but not limited to." The term "and/or", as used herein, is intended to refer to either or both of the elements so conjoined. The phrase "at least one" in reference to a list of one or more elements, is intended to refer to at least one element selected from any one or more of the elements in the list of elements, but not necessarily including at least one of each and every element specifically listed within the list of elements. Thus, as a non-limiting example, the phrase "at least one of A and B" may refer to at least one A with no B present, at least one B with no A present, or at least one A and at least one B in combination. In the context of describing the combining of components by the "addition" or "adding" of one component to another, or the separating of components by the "removal" or "removing" of one component from another, those skilled in the art will understand that the order of addition/removal is not critical (unless stated otherwise). The terms "remove", "removing", and "removal", with reference to one or more impurities, contaminants, and/or constituents of biogas, includes partial removal. The terms "cause" or "causing", as used herein, may include arranging or bringing about a specific result (e.g., a withdrawal of a gas), either directly or indirectly, or to play a role in a series of activities through commercial arrangements such as a written agreement, verbal agreement, or contract. The term "associated with", as used herein with reference to two elements, is intended to refer to the two elements being connected with each other, linked to each other, related in some way, dependent upon each other in some way, and/or in some relationship with each other. The terms "first", "second", etc., may be used to distinguish one element from another, and these elements should not be limited by these terms. The term "plurality", as used herein, refers to two or more. The term "providing" as used herein with respect to an element, refers to directly or indirectly obtaining the element and/or making the element available for use. The terms "upstream" and "downstream", as used herein, refer to the disposition of a step/stage in the process with respect to the disposition of other steps/stages of the process. For example, the term upstream can be used to describe to a step/stage that occurs at an earlier point of the process, whereas the term downstream can be used to describe a step/stage that occurs later in the process. Unless defined otherwise, all technical and scientific terms used herein have the same meanings as commonly understood by one of ordinary skill in the art.

The instant disclosure describes certain embodiments of system(s) and/or processes related to the anaerobic digestion of bales of cellulosic biomass for producing biogas, wherein the anaerobic digestion is a liquid anaerobic digestion. The term "liquid anaerobic digestion", as used herein, refers to an anaerobic digestion wherein aqueous liquid is added (e.g., before, during, and/or after the bales are loaded into the anaerobic digester) to a level selected such that at least some bales loaded into the anaerobic digester, which are in direct contact with the liquid, are fully submerged below a surface of the liquid (e.g., are suspended within the liquid or rest at the bottom of the anaerobic digester) or float near the surface of the liquid.

In such embodiments, the system(s) and/or process(es) provide various advantages over the wet anaerobic digestion of loose (unbound) cellulosic biomass. For example, consider the following comparative example for the wet anaerobic digestion of loose straw. Bales of straw are transported to the processing site and are stored until needed. At periodic intervals, the baled straw is unbaled and subjected to size reduction (e.g., chopped). The straw may be unbaled manually or using a straw bale breaker. For example, the straw bales may be placed on a straw conveyer and fed to a bale breaker. After the initial size reduction (e.g., chopping), the straw is pretreated. The first stage of the pretreatment is to feed the straw into a hammer mill that breaks the tubular structure of the straw to prevent floatation. Optionally, the pretreatment includes sand removal as a sand build up may disrupt the process over time. Optionally, the pretreatment also includes chemical and/or biological pretreatment as straw may be slow to digest without chemical and/or biological pretreatment. The unbaled and/or pretreated straw may be stored for some time so that there is a substantially continuous supply of feedstock available for anaerobic digestion. The processing of the chopped straw typically includes preparing a slurry of the pretreated straw. The pretreated slurry is continuously pumped into a cylindrical anaerobic digester, which has steel or concrete walls and is equipped with a stirring mechanism. For the anaerobic digestion, the contents of the anaerobic digester are heated to about 35° ° C. and maintained at a pH between about 6.6 and about 7.6.

In this comparative example, the total solids within the anaerobic digester is between 5% and 10%, the size of the straw particles is less than 3 cm long (e.g., typically under 1 cm), and the contents of the anaerobic digester are slowly stirred to maximize contact of the microorganisms with the substrate, to prevent the formation layers (e.g., including floating layers and sediment layers), and/or to avoid forming scum at the surface. The retention time of straw in this continuous anaerobic digestion is between about 10 and 25 days (e.g., typically about 18-20 days). Biogas is collected from the anaerobic digestion. In general, when there are large quantities of straw to digest (i.e., when the anaerobic digestion is conducted on a relatively large scale), the preparatory process can require special feeding systems and is associated with significant costs (e.g., including storage costs).

In contrast to the comparative example, certain embodiments of the instant disclosure relate to the anaerobic of cellulosic biomass that is baled for at least part of the anaerobic digestion (e.g., a first part). Subjecting bales of cellulosic biomass to an anaerobic digestion exploits the compact nature of the bales (e.g., increases the amount of straw that can be treated within each anaerobic digester), obviates conventional processing of the bales of cellulosic biomass (e.g., unbaling, size reduction, pretreatment, and/or slurrying), and/or reduces some of the challenges associated with stirring (e.g., limited digester volume, excessive energy consumption, maintenance associated with the stirring mechanism and/or abrasion in the reactor from sand and grit). Stirring is particularly challenging and/or costly for large-scale anaerobic digesters as agitation at this scale typically requires very large cylindrical vessels with strong walls and/or infrastructure to support the agitators. For example, while small-scale anaerobic digesters (e.g., used for small farms) are often made from plastic, large-scale anaerobic digesters are often made from concrete, carbon steel, and/or stainless steel. The vertical steel walls used for large-scale anaerobic digestion can be very thick and/or require difficult machining.

In addition to increasing the feedstock loading per anaerobic digester, providing baled feedstock for anaerobic digestion also opens up the possibilities of types of anaerobic digester that can be used. While the use of large-scale anaerobic digesters fabricated with vertical steel walls is common for large-scale operations, such anaerobic digesters may be expensive to fabricate and/or install, may have a limited lifetime (e.g., due to corrosion, pitting, etc.), and/or may be associated with operational challenges and/or high operational costs (e.g., maintaining the anaerobic digester within a certain pH range and/or heating the contents to maintain it within a certain temperature range). As described herein, the anaerobic digestion of baled feedstock does not need to be conducted in cylindrical vessels with steel walls, but instead can be conducted in any suitable enclosure (e.g., vessel, vat, pit, pond, basin, lagoon, pool, etc.) that can hold water and is covered, or can be covered, to provide anaerobic conditions. Utilizing a lagoon type anaerobic digester (e.g., having simple lined walls) can simplify the process. While lagoon type anaerobic digesters have been used for waste treatment, their use for biogas production from loose cellulosic biomass such as straw is not ideal. For example, without stirring, the loose fibers can fall to bottom of the lagoon and be compacted by the weight of other fibers settling thereon, which can make it challenging for the microorganisms to reach the substrate. However, by subjecting bales of cellulosic material (e.g., intact bales) to anaerobic digestion in a lagoon type digester, the shape of the bales may permit access of water, nutrients, and/or microbial inoculum, at all levels within the anaerobic digester (e.g., for at least for part of the anaerobic digestion), even the bottom, without stirring.

According to an embodiment of the instant disclosure, there is provided a process for converting cellulosic biomass to fuel, chemical(s), and/or products, the process comprising:

(a) loading bales of cellulosic biomass into an enclosure;
(b) at least partially filling the enclosure with an aqueous liquid, wherein the aqueous liquid is filled to a level selected to at least partially submerge the bales of cellulosic biomass once loaded into the enclosure;
(c) providing anaerobic conditions within the enclosure;
(d) subjecting the bales loaded within the enclosure to an anaerobic digestion to produce biogas, the biogas comprising methane, the anaerobic digestion producing digestate; and,
(e) collecting at least a portion of the biogas produced from the anaerobic digestion of the bales of cellulosic biomass.

The bales of cellulosic biomass can be loaded into the enclosure when the enclosure is void of liquid or contains liquid (e.g., of any amount). It can be advantageous to load the bales of cellulosic biomass into the enclosure when there is little to no liquid (e.g., under 30 cm). For example, with little to no liquid in the enclosure, the bales can be moved into the enclosure by vehicle, can be distributed evenly, and/or can be readily stacked in any configuration. It can be particularly advantageous to load the bales into the enclosure by driving the bales into the enclosure (e.g., using a vehicle), where they are unloaded manually or mechanically. In general, any suitably designed equipment (e.g., bale handling) and or vehicles can be used for loading the bales into the enclosure. For example, the bales may be transferred and/or stacked using any combination of a forklift, a bale lifter, a tractor (e.g., front end loader), telescopic handler, truck, trailer, etc. Bale handling equipment can be useful regardless of the size of the bales as many bales may be loaded into each enclosure. In one embodiment, more than about 100, 200, 300, 400, 500, 600, 700, 800, 900, or 1000 bales are loaded into each enclosure. Since bale handling equipment is typically required upstream of the anaerobic digestion to unload the transported bales and/or stack the bales so they can be stored until needed, the same equipment can be used to load the bales into the enclosure and/or stack the bales within the enclosure. Accordingly, there is significant cost savings relative to the comparative example, which requires a straw conveyer, bale breaker, hammer mill, pretreatment equipment, more conveying equipment, etc. In addition, there is significant cost savings related to the digester itself. For example, unlike the comparative example, which can require a cylindrical digester with stirring, the digester(s) for digesting bales of cellulosic biomass can have any shape (e.g., rectangular or cylindrical) and can have walls made of any suitable material (e.g., dirt, clay, concrete, plastic, etc.).

The liquid can be introduced into the enclosure prior to loading the bales, while loading the bales, and/or after loading the bales into the enclosure. The liquid is added in an amount (e.g., to a level) such that the bales that are in the enclosure and/or will be loaded into the enclosure are in free liquid and can be at least partially submerged below a surface level of the free liquid. The term "at least partially submerged," as used herein, with reference to a bale, refers to the bale, which is in direct contact with free liquid, at least partially descending below the surface level of the free liquid. For example, a bale that is at least partially submerged within a liquid can be fully submerged below the surface of the liquid (e.g., be suspended or be at the bottom of the enclosure) and/or can float near the surface of the liquid (e.g., with some of the bale above the liquid level). The term "free liquid", as used herein, refers to the liquid outside of the bales (i.e., not within the nominal volume of the bales). In general, the liquid is an aqueous liquid. The term "aqueous liquid", as used herein, refers to liquid made with or containing water (e.g., can be water or can be a solution). Any number of components can be added to bring the liquid to the desired level. For example, the liquid can include water, chemicals, liquid nutrients, and/or microbial inoculum. Such components can be added together or individually, over any length of time throughout the anaerobic digestion. For example, the chemicals added may be acids and/or bases selected to adjust the pH of the contents of the digester. Such chemicals can be added proactively and/or in response to changing conditions (e.g., changing pH). In some cases, a high solids loading can result in organic acid accumulation, which can reduce the pH and/or sour the digester. Adding base (e.g., lime solution) can increase the pH. Adding ammonia ($NH_3$) or urea may increase the pH and/or increase the C/N ratio within the digester (e.g., a low C/N ratio may limit biogas production). In one embodiment, the aqueous liquid is a basic solution and/or contains added base.

In general, the contents of the enclosure are inoculated for the anaerobic digestion. Inoculating the contents of the enclosure refers to adding inoculum, which provides the microbial population for the anaerobic digestion. More specifically, the inoculum includes any suitable microorganisms provided in any suitable medium (e.g., a liquid or solid medium). For example, the inoculum can include one or more types of microorganisms (e.g., acid forming bacteria and methanogenic bacteria), each of which can be mesophilic or thermophilic (e.g., mesophilic or thermophilic bacteria), and which can be obtained from a cultured source (e.g., fresh culture, which can be genetically engineered) and/or a natural source (e.g., manure, digestate, etc.). It can be particularly advantageous to recuperate at least part of the digestate from each anaerobic digestion for use as inoculum in the same or another digestion. When digestate is used to inoculate the contents of the digester, the inoculum can include any part of the digestate including the liquid and/or solids. For example, in some embodiments, dewatered solids from the digestate of one digestion is diluted and stored for use with a new batch of bales. In one embodiment, liquid from the digestate is used to provide the inoculum. Using liquid digestate as an inoculum is advantageous as it can reduce water usage. Inoculums for anaerobic digestion are well known, and one skilled in the art will be able to select the appropriate inoculum and/or amount of inoculum added for the given operating conditions (e.g., for a given amount of feedstock held in the digester, the amount of water added to the digester, temperature, retention time, etc.). Preferably, the inoculum is added in an amount sufficient to at least partially anaerobically digest the bales and produce a collectable amount of biogas. The inoculum can be added prior to loading the bales into the enclosure, as the bales are loaded into the enclosure, and/or after the bales have been loaded into the enclosure. The inoculum can be added prior to or after filling the enclosure with water or can be added with the water. The inoculum can be added to the enclosure (e.g., to the bottom), spread/sprayed on top of the bales, and/or injected within the bales. In one embodiment, inoculum is injected into one or more bales, or each bale, prior to loading the bales into the enclosure or as the bales are stacked within the enclosure. In one embodiment, water, an aqueous solution, and/or chemicals (e.g., ammonia) is alternatively or additionally injected into one or more bales, or each bale, prior to loading the bales into the enclosure or as the bales are stacked within the enclosure. In one embodiment, one or more bales, or each bale, is submerged (e.g., soaked) in an aqueous liquid containing inoculum prior to being loaded into the enclosure. In one embodiment, each bale is injected with an aqueous liquid containing inoculum using vacuum impregnation, wherein a vacuum is drawn prior to adding the inoculum. For example, vacuum impregnation may be achieved using equipment used in the pulp and paper industry.

The anaerobic digestion can be conducted in batch mode and/or continuous mode. In batch mode, the bales of cellulosic biomass are loaded into the enclosure at the start of the process. Once the liquid and bales have been added to the enclosure, the enclosure is then sealed (i.e., to provide the anaerobic conditions). Alternatively, the enclosure can be sealed before the liquid and/or bales are added to the enclosure (e.g., after the bales are added, but prior to the bulk of the liquid being added). The term "seal", as used herein with reference to the enclosure, refers to providing a barrier (e.g., cover, closed door, etc.) that limits the amount of oxygen that can enter the digester, thereby providing the anaerobic conditions, and/or substantially prevents biogas from escaping to the atmosphere. Inoculum, nutrients, and/or chemicals can be added prior to starting the anaerobic digestion (e.g., prior to sealing the enclosure) and/or at one or more points in the anaerobic digestion (e.g., to reseed the digester in response to dropping biogas production). Biogas is collected as it is produced. After anaerobic digestion is complete, digestate is removed from the enclosure. The material used to secure the bales (e.g., twine) can be removed from the digestate prior to removing the digestate from the enclosure and/or after removing the digestate from the enclosure, if it has not been digested. The term "digestate", as used herein, refers to the material remaining at the end of the anaerobic digestion. The end of the anaerobic digestion can be dependent on the selected process. For example, in many cases the end of the anaerobic digestion may be after biogas production peaks and after it falls below some predetermined level. In other cases, the end of the batch anaerobic digestion may be when the bales have reached a level of digestion that facilitates a second stage of anaerobic digestion. For example, a first stage of digestion at mesophilic temperatures may be complete when a certain concentration of acetic acid is produced. The bales are then transferred to a second stage at higher temperature for methane production. Alternatively, the mesophilic digestate is removed while the bales remain in the enclosure, and digestate from a second stage is added to the enclosure for the second stage of anaerobic digestion. Two-stage anaerobic digestions are well known in the art and may be conducted in or more enclosures. As will be understood by those having ordinary skill in the art, biogas production often follows a normal distribution pattern over time, and this distribution pattern can be used to predict when the anaerobic digestion is complete.

In general, digestate can have a liquid component and/or a solid component. The digestate can be removed from the enclosure using any suitable method or combination of methods. For example, at least a portion of the digestate can be removed by draining the digester (e.g., to a certain level using gravity, one or more pumps, and/or a conveyor). Any sediment (e.g., solid digestate) remaining after liquid has been removed from the digester can be removed using any suitable method and/or systems (e.g., by shoveling, one or more front end loaders, a conveyance member, etc.). In some cases, it can be advantageous to provide a solids liquid separation as the digestate is removed from the enclosure. For example, in one embodiment, the digestate is withdrawn from the enclosure (e.g., pumped out) and fed to a screw press or decanter centrifuge to produce a solid stream and a liquid stream. In one embodiment, the digestate is withdrawn from the enclosure and fed to a screw press. At least some of the solid and/or liquid digestate can be retained to inoculate another batch of bales, can be applied to the field (e.g., as a nutrient rich fertilizer, organic rich compost, or as a soil amendment), and/or can be further treated (e.g., solids may be processed to provide animal bedding). In general, the liquid and solid components may be separated and handled independently, as each may have value that can be realized with varying degrees of processing, or may be kept together. In one embodiment, the solid digestate is applied to the fields. In one embodiment, the solid digestate is used to produce animal bedding. In one embodiment, the solid digestate is subjected to hydrothermal liquefaction to produce bio-oil, which is used as and/or processed to produce a fuel, or which can be stored as part of a carbon capture and storage (CCS) process. In one embodiment, the solid digestate is subjected to hydrothermal liquefaction to produce bio-oil and/or char, and the char applied to land and/or is part of a CCS process.

Advantageously, this batch process is relatively simple and requires less equipment and lower levels of design work compared to the comparative example. Accordingly, it can be more cost effective. For example, it does not require stirring and/or the associated equipment. Further advantageously, this batch process facilitates loading the bales into the enclosure and/or removing the solid digestate by vehicle (e.g., front end loader). For example, the solid digestate can be unloaded in bulk and transferred to storage, a field, a further treatment, etc., by vehicle. In view of the relatively simple digester, absence of stirring, and/or efficient transfer of feedstock/digestate, this process may be readily scaled up (e.g., by providing a relatively large enclosure and/or by providing multiple enclosures). For example, it can be advantageous to provide multiple enclosures in order to provide a constant supply of biogas.

In continuous mode, the bales of cellulosic biomass are loaded into the digester throughout the process (e.g., constantly or periodically), while digestate is also removed throughout the process (e.g., constantly or periodically). In general, the start-up of the continuous anaerobic digestion will be similar to the batch process. However, once the anaerobic digestion reaches a certain level, new bales are loaded into the digester (e.g., periodically). More specifically, the new bales are loaded into the digester such that they displace digestate, which is removed from the digester.

In one embodiment, the continuous mode anaerobic digestion is a continuous plug flow digestion. A continuous plug flow digestion can be modeled with the plug flow reactor model. For example, a bale of cellulosic biomass loaded into such an anaerobic digestion can be viewed as traveling some distance before it leaves as digestate. The length that the bale travels and/or flow rate are selected such that the cellulosic material in each bale is substantially digested after propagating through the digester and can be removed as digestate. For example, although plug flow digesters can be any shape, they are often at least 5 times longer than they are wide. The flow can be provided by forcing the bales into the digester using any suitable equipment (e.g., providing a pushing mechanism) and/or by providing any suitable mechanism that conveys the bales along the digester. In some cases, the bales may be sufficiently buoyant that withdrawing digestate at the end of the elongated digester moves the bales (e.g., along the channel). Although the digesters disclosed herein do not require mechanical stirring of the cellulosic biomass, in some embodiments, stirring and/or agitation is provided (e.g., using pumps, paddles, injected gas, etc.). In one embodiment, liquid is moved within the enclosure relative to the bales (e.g., using pumps, paddles, injected gas, etc.).

Advantageously, this continuous process is relatively simple and requires less equipment and lower levels of design work compared to the comparative example. Accordingly, it can be more cost effective. For example, it does not require stirring of the cellulosic biomass and/or the associated equipment. Further advantageously, this continuous process facilitates loading the bales by vehicle (e.g., front end loader). In view of the relatively simple digester, possible absence of stirring, and/or efficient transfer of feedstock/digestate, this continuous process may be readily scaled up (e.g., by providing a relatively large digester). Relative to the batch process, this continuous process is advantageous in that there is a relatively constant production of biogas, that the conditions are relatively stable for the microorganisms (e.g., the microorganisms do not have to adapt to new conditions as they do for the start-up of a new batch), and/or that there may be a higher biogas yield. In addition, it can provide a relatively constant supply of solid and/or liquid digestate. In continuous mode, the end of digestion typically corresponds to when the cellulosic biomass has travelled the length of the enclosure. As the digestate is removed, it can be pumped to a solids/liquid separation (e.g., screw press or decanter centrifuge) to provide a solids stream and a liquid stream. At least a portion of the liquid stream can be reintroduced into the digester and/or applied to land. At least a portion of the solids stream can be applied to the land and/or used to produce a product (e.g., animal bedding). In one embodiment, the anaerobic digestion is conducted in continuous mode and least 50%, at least 60%, at least 70%, at least 80%, or at least 90% of the liquid digestate is reintroduced back into the same digester or another digester (e.g., to reduce the amount of fresh water added to the process).

Regardless of whether the anaerobic digestion is conducted in batch or continuous mode, such process(es)/system(s) provide many advantages, including the cost advantages for large scale operation (e.g., more than about 100 bales per batch). In addition, since the bales can maintain their shape for at least part of the anaerobic digestion (e.g., at least the first quarter of the retention time, or even at least half of the retention time), this may prevent problems associated with settling and/or stratification during the early part of the digestion even in the absence of stirring. For example, since the cellulosic biomass is baled, sand/fines associated with the cellulosic material may not settle to the bottom until the later stages of the digestion when the bales begin to fall apart. Since the anaerobic digestion is conducted on bales of cellulosic biomass, the pretreatment costs, feedstock handling costs, and/or mixing costs, may be reduced. Another potential advantage of subjecting bales of cellulosic biomass to anaerobic digestion in a large digester is that it may obviate the need to provide heat. More specifically, heat generated during the digestion of the relatively dense cellulosic biomass may provide the contents of the enclosure with a sufficient amount of heat to obviate the need for external heat sources, even when the ambient air temperature is below 0°. In some cases, the heat may even build up within each bale, thereby providing heat for thermophilic microorganisms, and increasing the rate of digestion. Yet another advantage of subjecting bales of cellulosic material to anaerobic digestion is that it may reduce storage costs. For example, it may be unnecessary to store loose cellulosic biomass (e.g., although it may be stored prior to bale formation in some cases). Furthermore, since the anaerobic digestion can be relatively slow (e.g., slow relative to the comparative example), the digester can function as both storage and treatment of the bales of cellulosic biomass.

The process(es)/system(s) disclosed herein that relate to the liquid anerobic digestion of bales of cellulosic materials also provide one or more advantages relative to a dry anaerobic digestion conducted on bales of cellulosic biomass. For example, conducting a liquid anaerobic digestion allows the liquid to facilitate movement of the bales for a continuous anaerobic digestion. In addition, the liquid can potentially reduce accumulation of toxic and inhibitory compounds.

Advantageously, in certain embodiments the process(es)/systems(s) described herein produce fuel. For example, the raw biogas collected from the anaerobic digestion is a fuel that can be used to produce heat and/or power, or that can be upgraded (e.g., to produce a transportation fuel such as RNG). Alternatively, or additionally, the raw or upgraded biogas can be used to produce fuel, chemicals, or other products. For example, in certain embodiments, the raw or upgraded biogas is used to produce fuel (e.g., one or more fuels such as hydrogen, gasoline, diesel, jet fuel, methanol, ethanol, etc.), chemical product (e.g., methanol, ammonia, fertilizer, etc.), or intermediates (e.g., methanol, hydrogen, ammonia, ethanol, etc.). In certain embodiments, the raw or upgraded biogas is used to produce hydrogen, which can be used, for example, in oil refining, ammonia production, fertilizer production, methanol production, and steel production.

Further advantageously, the fuel, chemical, or other products can have lifecycle greenhouse gas (GHG) emissions and/or carbon intensity that is relatively low (e.g., compared to the corresponding fuel, chemical, or other product produced from fossil sources). The relatively low lifecycle GHG emissions and/or carbon intensity may be at least partially dependent on using a feedstock that is an agricultural residue or energy crop, energy savings resulting from the process (e.g., generating heat during anaerobic digestion instead of requiring heat) and/or as a result of one or more steps to reduce carbon intensity (e.g., using renewable and/or low carbon power or employing CCS). In one embodiment, carbon dioxide ($CO_2$) produced during the anaerobic digestion is captured and stored, thereby reducing the carbon intensity of fuel produced from the process (e.g., the upgraded biogas and/or fuel produced therefrom). In one embodiment, carbon containing material obtained or derived from the digestate is provided for storage as part of CCS. The carbon containing material can be obtained and/or produced by processing the digestate. For example, digestate can be subjected to a hydrothermal liquefaction to provide a bio-oil that can be sequestered. In some cases, the sequestration method is selected to prevent biodegradation of the material and/or trap GHGs in the event of biodegradation. In some cases, the material is treated in a process to reduce the potential for biodegradation. Advantageously, storing a liquid or solid by-product produced from the process as part of CCS can further reduce the carbon intensity of the fuel, chemical, or other product.

The instant disclosure also describes certain embodiments of system(s) and/or processes related to processing the digestate from the anaerobic digestion of cellulosic biomass via hydrothermal liquefaction (e.g., either baled cellulosic biomass or unbaled cellulosic biomass (e.g., mechanically pretreated).

Cellulosic Biomass

In general, the feedstock for the anerobic digestion is cellulosic biomass. In certain embodiments, the feedstock for the anerobic digestion is straw. Using straw as a feedstock for anaerobic digestion is advantageous because it can be widely available, can be relatively inexpensive, and can have a relatively high biogas production potential. Moreover, when straw is used to produce biogas, the fuel, chemicals, or products produced from the biogas, can be derived from what may be considered waste.

In certain embodiments, the cellulosic biomass is baled for the anerobic digestion. In general, the bales can be formed from any cellulosic biomass that can be provided as a bale. A bale generally refers to bundle of material that has been tightly bound and thus can be moved and/or stored more efficiently (e.g., without substantially falling apart and/or losing its shape). Bales are typically formed by compressing the material and securing it in its compressed state (e.g., with twine, wire, netwrap, etc.). While any material may be used to bind the bales, it can be advantageous to select a material that allows liquid to permeate the bale, can be readily removed at the end of the anaerobic digestion, and/or is biodegradable. In one embodiment, the binding material is sisal twine, plastic twine, and/or biodegradable twine.

The bales can be formed using any suitable method, including the use of commercial balers. Commercial balers are often used to gather cut crop material and secure it together in bundles. The crops can be cut and left in the field in windrows to dry, and once dry, can be collected by a baler. Alternatively, the crops can be cut and baled directly. Crops are often collected and baled during or after grain harvest. For example, in one embodiment, a grain crop is cut and baled directly after some preliminary processing to separate the grain from the rest of the plant. Straw balers and/or baling technologies for use in the embodiments described herein can be selected readily by those skilled in the art based on the description herein.

The bales of cellulosic biomass may be of any suitable size and/or shape. For example, bales are often rectangular or cylindrical (i.e., so called "round" bales). For example, the bales could range from small rectangular bales (e.g., having dimensions of approximately 45 cm×36 cm×92 cm) to large rectangular bales (e.g., having dimensions of approximately 2.4 m×1.2 m×1.2 m), or could range from small round bales (e.g., having a diameter of about 1.2 m and a width of about 1.2 m) to large round bales (e.g., having a diameter of about 1.8 m and a width of about 1.5 m). Some examples of suitable rectangular bales, include but are not limited to, about 4'×4'×4' (~1.2 m×1.2 m×1.2 m), about 3'×3'×8' (~0.9 m×0.9 m×2.4 m), about 4'×3'×8' (~1.2 m×0.9 m×2.4 m), about 4'×4'×8' (~1.2 m×1.2 m×2.4 m), or about 14"×18"×40" (~0.4 m×0.5 m×1 m). Providing bales having at least one dimension of at least about 8" (20 cm), at least about 12" (30 cm), or at least about 18" (46 cm) can be particularly advantageous. For example, in one embodiment, each bale is a rectangular bale having dimensions of about 50 cm(±10 cm)×50 cm(±10 cm)×100 cm. In one embodiment, at least 50% of the bales in a digester has a dimension that is at least about 1' (30 cm), at least about 2' (61 cm), or at least about 3' (91 cm). In one embodiment, the smallest dimension (i.e., height, length, width, or radius) of at least 50% of the bales is at least about 1' (30 cm), at least about 2' (61 cm), or at least about 3' (91 cm). In one embodiment, the bales have an average nominal volume (e.g., height×length×width) of at least about 30 L, at least about 40 L, at least about 50 L, at least about 60 L, at least about 70 L, at least about 80 L, at least about 90 L, or at least about 100 L. The feedstock particles/shreds used to form the bales can be of any length. In one embodiment, the average length of the feedstock particles is between about 10 cm and about 30 cm (e.g., average of about 20 cm). In one embodiment, the average length of the feedstock particles is at least about 10 cm, at least about 15 cm, at least about 20 cm, or at least about 25 cm.

In general, the bales may be of any suitable density and/or have any suitable moisture content. The density of the bales may be dependent on the type of cellulosic biomass, whether it is fresh or dried, and/or the degree of compaction (e.g., from the baling technique). For example, the density of round bales can be similar to that of conventional rectangular bales, but lower that of big squares. Straw bales often have a density between about 100 and about 250 kg/$m^3$, and more commonly, between about 150 and about 200 kg/$m^3$. Preferably, the density of the bales allows at least some liquid to permeate therein and/or is less than that typical density of a briquette (e.g., less than 350 kg/$m^3$). In one embodiment, the bales have a density between about 80 and about 300 kg/$m^3$, about 80 and about 275 kg/$m^3$, between about 80 and about 250 kg/$m^3$, between about 90 and about 240 kg/$m^3$, between about 90 and about 230 kg/$m^3$, between about 100 and about 220 kg/$m^3$, between about 110 and about 220 kg/$m^3$, between about 120 and about 210 kg/$m^3$, between about 120 and about 200 kg/$m^3$, or between about 150 and about 200 kg/$m^3$. In one embodiment, the bales have a density not more than about 300 kg/$m^3$, not more than about 310 kg/$m^3$, not more than about 320 kg/$m^3$, not more than about 330 kg/$m^3$, not more than about 340 kg/$m^3$, not more than about 300 kg/$m^3$, not more than about 280 kg/$m^3$, or not more than about 250 kg/$m^3$. The moisture content of bales may vary depending on the feedstock, storage conditions, and age of the bale. For example, the moisture content of straw bales is often between about 5% to about 50%. The density of the bales is determined prior to any processing that adds liquid.

In one embodiment, the cellulosic biomass is lignocellulosic biomass. Lignocellulosic biomass is primarily composed of polysaccharides (i.e., cellulose and hemicellulose) and aromatic polymer (i.e., lignin). For example, lignocellulosic biomass often has cellulose in an amount greater than about 25%, hemicellulose in an amount greater than about 15%, and lignin in an amount greater than 15% lignin, by weight (w/w). In one embodiment, the feedstock has a combined content of cellulose, hemicellulose and lignin greater than 25% (w/w).

In one embodiment, the cellulosic biomass is obtained from a field crop (e.g., is an energy crop or agricultural crop residue). Field crops are particularly advantageous as they can be baled in the field to facilitate transport.

In one embodiment, the cellulosic biomass is an energy crop. Energy crops are non-food crops that can be grown on marginal land (land not suitable for traditional food crops like corn and soybeans) specifically for fuel and/or energy production. For example, in one embodiment, the feedstock is a cellulosic grass or reed. In one embodiment, the feedstock is selected from miscanthus, giant reed grass (*Arundo donax*), reed canary grass, switchgrass, hemp energy cane, sorghum (including sweet sorghum), cord grass, and/or rye grass.

In one embodiment, the cellulosic biomass is an agricultural crop residue. Agricultural crop residues, which are often considered waste products and/or byproducts of crop production, may be used to produce biofuels without concerns about the feedstock competing with food crops for arable land. Agricultural crop residues can refer to field residues or processing residues. Field residues, which are materials left after harvesting a crop (e.g., left in an agricultural field or orchard), can include straw, stubble, stover, etc. The term straw refers to the stalk/stem of cereal plants and grasses after the removal of the grain and chaff (e.g., after threshing). The term stover refers to the leaves and stalks of field crops such as corn (maize), sorghum, or soybean that are commonly left in a field after harvesting the grain (e.g., includes stalks, leaves, husks, and cobs). Process residues are materials left after the crop is processed into a usable resource (e.g., sugar cane bagasse). In one embodiment, the feedstock is an agricultural crop residue selected from soybean stover, corn stover, rice straw, sugar cane tops and/or leaves, sugar cane bagasse, rice straw, barley straw, wheat straw, canola straw, oat straw, and/or any cereal grain straw.

In one embodiment, the cellulosic biomass is fibrous biomass. The term "fibrous biomass", as used herein, refers to biomass originating from plants having a fibrous particle that can be compressed (e.g., baled). Some examples of fibrous feedstock include dedicated energy crops and agricultural resides (e.g., straw and/or stover). In one embodiment, the feedstock is straw (e.g., wheat straw, oat straw, and/or rice straw). In one embodiment, the feedstock is an energy crop. In one embodiment, the feedstock is grass, weeds, or stalks (e.g., corn stalks).

Using baled feedstock such as agricultural residues and/or energy crops is particularly advantageous as such feedstocks can have a relatively high potassium ash content. In contrast to conversions based on the thermal treatment of such feedstocks, wherein the potassium ash may be associated with fouling and/or slagging issues, the alkali in the potassium ash may be beneficial for anaerobic digestion. In embodiments where the feedstock is baled, less alkali is removed during processing. In one embodiment, the feedstock has a potassium bicarbonate ($KHCO_3$) concentration of at least 1% by weight on a dry basis. A $KHCO_3$ concentration of at least 1% by weight can provide buffering, which may help control the pH. In one embodiment, $KHCO_3$ is added in an amount sufficient to provide the liquid with a pH within a certain range (e.g., 7.4-8).

In general, the bales may include one or more types of cellulosic biomass. For example, the bales provided for anaerobic digestion can include different types of feedstock (e.g., bales of straw and bales of energy crops). Providing baled feedstock for anaerobic digestion facilitates treating a greater mass of feedstock (on a dry basis) per digester volume. The term "baled feedstock", as used herein, refers to feedstock that has been bundled to provide a bale. The term "digester volume", as used herein, refers to the water volume that the digester can hold. Baling the feedstock in the field can facilitate transport of the feedstock to the processing site. In some embodiments, feedstock baled in the field is transported to a processing site, where the bales are cut into two or more sections for the anaerobic digestion. In such embodiments, each section is a bale if it remains tightly bound (e.g., is a bundle that does not substantially fall apart and/or lose its shape upon being loaded into the anaerobic digester). In some embodiments, the bales loaded into the enclosure have had some or all of the binding removed (e.g., prior to loading the bale into the enclosure or after loading the bale into the enclosure), but are loaded and/or stacked within the enclosure such that they substantially retain their baled form (i.e., for at least an initial part of the anaerobic digestion).

In some embodiments, each bale is processed for anaerobic digestion (e.g., upstream of anaerobic digestion). For example, such processing can include soaking each bale in water (e.g., to saturate each bale with water), soaking each bale in an aqueous solution (e.g., basic), soaking each bale in an inoculum containing liquid, injecting steam and/or a chemical into each bale (e.g., $NH_3$), injecting inoculum into each bale, drawing a vacuum on each bale, and/or perforating each bale. With regard to the latter, punching, drilling, and/or boring one or more holes into and/or through each bale can allow water, nutrients, and/or microbial inoculum to reach the center of each bale faster, may reduce buoyancy of the bales, and/or may even out temperature fluctuations within each bale. Punching, drilling, and/or boring one or more holes through each bale can facilitate the use of one or more guides (e.g., ropes, wires, bars, etc.) that can be fed through the holes and used to direct motion of the bale in a certain direction and/or prevent motion of the bale in certain direction. For example, horizontal guide lines may be used to ensure bales are submerged and/or to provide smooth movement of bales along a channel. In certain embodiments, the guides are hollow tubes having one or more holes for providing chemicals/or inoculum into the bales (e.g., the bales can be soaked in water for a given time, and then inoculum can be injected into the bales via the hollow tubes). In one embodiment, the processing of the bales drives air out of the bales, thereby reducing the risk of accidental oxygen loading into the anaerobic digester. For example, the air may be driven out by injecting steam or chemicals into the bales, by immersing the bales in liquid (e.g., cold, warm, and/or hot), and/or or by pulling a vacuum on the bale. In one embodiment, processing the bales for anaerobic digestion includes inoculating the bales (e.g., by impregnating with digestate liquor), adjusting the C:N ratio (e.g., by adding ammonia or urea), and/or adjusting the pH (e.g., by recycling $KHCO_3$ in digestate liquor). In this embodiment, the temperature may or may not be adjusted.

Anaerobic Digestion

In general, the cellulosic biomass (e.g., bales) are subjected to anaerobic digestion in one or more anaerobic digesters. The term "anaerobic digester", as used herein, refers to a system designed and/or configured to function as a biological reactor that facilitates anaerobic digestion. The term "anaerobic digestion", as used herein, refers to a series of processes in which microorganisms break down organic material under anaerobic conditions resulting in the production of biogas. For example, the stages of anaerobic digestion typically include hydrolysis, acidogenesis, acetogenesis, and methanogenesis. Microorganisms participating in one or more of these stages can include acid forming bacteria (acetogens) and methane forming archaea (methanogens).

In general, the process includes providing anaerobic conditions. Since oxygen is generally considered inhibitory and/or toxic to anaerobic microorganisms (e.g., acetogens and methanogens), anaerobic digesters are often designed to operate with little to no dissolved oxygen. However, some amount of oxygen may enter the anaerobic digester unintentionally, and in some cases, it has been found that adding small amounts of oxygen can be beneficial (e.g., some amount of oxygen can be introduced to a basically anaerobic process). The term "anaerobic conditions", as used herein, refers to conditions where there is little to no oxygen (i.e., oxygen limited conditions) and that enable biogas production. The anaerobic conditions can be achieved by providing a reasonably high operating depth (e.g., at least 3 to 5 meters), sealing the anaerobic digester to prevent oxygen from entering the anaerobic digester during the anaerobic digestion, adding a sweep gas such as nitrogen to the digester, and/or removing air from the bales prior to the anaerobic digestion (e.g., by soaking them in cold, warm, or hot liquid, injecting a gas or liquid therein, and/or pulling a vacuum on the bales).

The microorganisms that break down the organic material in the anaerobic digestion can be added at the start of each process and/or throughout each process. The source of the inoculum can be any digestate (e.g., sludge) from a natural or engineered project that contains a viable microbial community (e.g., includes self inoculation). For example, the inoculum can be obtained from sewage sludge, cattle slurry, municipal wastewater treatment plant sludge, or digestate from the anaerobic digestion of agricultural residues or energy crops. In general, the inoculum can provide the microorganisms in any suitable medium (e.g., a liquid or solid medium). Nutritional balance, pretreatment, and/or incubation may be provided.

The anaerobic digestion is conducted for a time and/or under conditions selected to promote the production of biogas. For example, in one embodiment, the anaerobic digestion is conducted for at least about 20 days, at least about 25 days, at least about 30 days, at least about 35 days, at least about 40 days, at least about 45 days, at least about 50 days, at least about 55 days, or at least about 60 days. In embodiments where the cellulosic biomass is digested at least partially when in bale form, it can be advantageous to provide retention times of at least about 30 days, more advantageously at least about 40 days, or even more than about 60 days. In one embodiment, the bales are subjected to anaerobic digestion without stirring and/or agitation for at least about 10 days, at least about 12 days, at least about 14 days, at least about 16 days, at least about 18 days, at least about 20 days, at least about 25 days, or at least about 30 days. In one embodiment, the anaerobic digestion is conducted for between about 40 days and 80 days, about 45 days and 75 days, between about 50 days and 70 days, about 50 days and 60 days, or between about 55 days and 65 days. While the digestion of bales of cellulosic biomass may take longer (e.g., 20-60 days) relative to the digestion of pretreated loose cellulosic biomass (e.g., about 20 days), the economic benefits of a simpler enclosure, absence of stirring, and/or increased scale are believed to outweigh the addition time and/or reduction in biogas production.

Factors affecting the anaerobic digestion process are known, and those skilled in the art can readily select process conditions to promote biogas production based on the description herein. For example, some conditions known to affect biogas production include pH, temperature, C/N ratio, salinity, toxin concentration, ratio of inoculum to biomass, dilution, etc. Some suitable ranges for such variables may include a pH range between about 6.6 and 7.6 (e.g., optimum around 7), a temperature range between about 20° C. and about 65° C. (e.g., optimum around 35° ° C. for a mesophilic system and 55° C. for a thermophilic system), a C/N ratio range between about 20 and 40 (e.g., optimum between 20 and 30), and/or a salinity range between about 0 and 8%. For example, at pH values lower than 5.5, acidogenic bacteria may be active but methanogenic bacteria may be inhibited. The digesting bales generate heat. The temperature can be controlled by withdrawing a portion of the liquor from the digester and cooling it (e.g., to about 20° C.) by heat exchange, then reintroducing the cool liquor to the digester. Another factor that can affect the anaerobic digestion is the solids consistency, herein also referred to as "consistency". The term "consistency", as used herein, refers to the mass of undissolved dry solids or "UDS" in a sample per mass of the sample, expressed as a weight percent (e.g., wt %). When determining the consistency at which the anaerobic digestion is conducted, the consistency is determined for the initial phase of the anaerobic digestion (i.e., is an initial consistency as the consistency will decrease as the anaerobic digestion progresses) and when the anaerobic digestion is conducted on bales of cellulosic biomass is determined for a sample size that includes multiple bales of cellulosic biomass. For example, the consistency of a batch process on bales of cellulosic biomass is preferably determined from at least the total mass of bales loaded into the enclosure, the average consistency of the bales loaded into the enclosure, and the total mass of liquid added to the enclosure. The consistency of a continuous process on bales of cellulosic biomass is determined from at least the total mass of bales loaded into the enclosure, the average consistency of the bales loaded into the enclosure, and the total mass of liquid added to the enclosure, over a given time period. The average consistency of the bales loaded into the enclosure is determined after any processing of the bales (e.g., after any impregnation with liquid) and is averaged over at least three bales. The consistency of each bale is determined from a representative sample that includes cellulosic biomass from a core of the bale and a surface of the bale. The mass of undissolved solids in the representative sample can be determined by filtering and washing the sample to remove dissolved solids and then drying the sample at a temperature and for a period of time that is sufficient to remove water from the sample, but does not result in thermal degradation of the sample. For example, 100 bales of 100 kg UDS each that have been impregnated with water to 12% consistency are added to an enclosure with equal weights of wet bales and free liquid. The weight of UDS is 10,000 kg. The weight of impregnated wet bales is 10,000/12%=83,333 kg. The weight of free liquid is also 83,333 kg, so the total initial weight is 166,666 kg. The consistency of the anaerobic digester is then 10,000 kg UDS/166,666 kg=6.0%. In one embodiment, the anaerobic digestion is conducted at a consistency between about 3% and about 15%, about 3% and about 12%, about 4% and about 12%, about 4% and about 10%, or about 5% and about 10%. Providing an amount of water to provide a consistency between about 5% and about 10% may provide a good compromise between reducing water usage and providing sufficient water. In one embodiment, the mass of free liquid added to the enclosure is at least about 50%, at least about 55%, at least about 60%, at least about 65%, at least about 65%, at least about 70%, at least about 75%, at least 80%, at least about 85%, at least about 90%, at least about 95%, or is at least about the mass of the wet bales loaded into enclosure. In one embodiment, the mass of free liquid added to the enclosure is at least about 50%, at least about 55%, at least about 60%, at least about 65%, at least about 65%, at least about 70%, at least about 75%, at least 80%, at least about 85%, at least about 90%, at least about 95%, or is at least about the UDS mass of the bales loaded into enclosure.

In general, each anaerobic digester includes an enclosure in which the anaerobic digestion is conducted and that can hold water (e.g., the enclosure can be a vessel, vat, pit, pond, basin, lagoon, pool, etc.). Such enclosures can have walls that are formed from natural (e.g., earthen berms) and/or artificial (e.g., concrete) materials, can be lined with natural (e.g., mud, clay, bentonite, etc.) and/or artificial (e.g., plastic, rubber, concrete, etc.) materials, and and/or can be of any shape (e.g., circular, rectangular, etc.). For example, in one embodiment, the enclosure includes a geomembrane liner. The enclosures can be fully above ground, partially above ground and partially below ground, or fully below ground level. Enclosures that extend at least partially below ground level are advantageous in terms of reducing construction costs. For example, referring to FIG. 1, an enclosure can be an earthen basin constructed by excavating part of the required volume 10 from below ground level 20, and using the excavated earth to build embankments (i.e., berms) 30 to provide the remaining digester volume 40. As will be understood by those skilled in the art, such earthen basins can be designed with any suitable area, depth, and/or wall slope. For example, the walls of such earthen basins may have slopes with a grade of 25% or 33% (i.e., θ=14° or 18°, respectively) and/or slopes with a grade up to 70% (i.e., θ=35°), or higher. In one embodiment, the anaerobic digestion is conducted in one or more earthen basins where θ is between about 30° and 40° (e.g., 35°). Providing relatively shallow slopes can reduce the risk of erosion and/or allow front end loader access within the basin. Providing relatively steep slopes can increase the volume within the enclosure while decreasing the land area required for the enclosure.

In one embodiment, the enclosure is a deep earthen basin (e.g., with a floor at least 3, 4, or 5 meters below ground level). In one embodiment, the enclosure has one or more concrete walls, each of which can be a vertical wall or a sloped wall, and which can be an above grade wall, a below grade wall, or a wall having above grade and below grade sections. For example, in some embodiments, the below grade wall height may be approximately the same as the above grade wall height. Concrete construction offers the advantage of added durability, stability of side slopes, and/or potential for vertical walls. Concrete construction may also facilitate the removal of solids with heavy equipment such as a front-end loader or tractor, which may drive into the enclosure. In one embodiment, the enclosure has concrete walls, and includes a sloped ramp for front-end loader access (e.g., the sloped access ramp forms one side of the enclosure, while the other walls are vertical or have relatively steep slopes). A ramp for front-end loader access can be advantageous not only for batch processes, wherein it can be used to load the bales into the enclosure and/or remove any digestate (e.g., not removed by draining and/or pumping), but also for continuous processes, where it can be used for start-up and/or periodic cleaning. In one embodiment, the enclosure has sloped concrete walls. In one embodiment, the enclosure has a substantially flat bottom.

As will be understood by those skilled in the art, the dimensions of the enclosure (e.g., length, width, and/or depth) and/or the slope of the walls can be dependent upon the construction materials used, the design of the enclosure, the local geography, and/or the scale at which the anaerobic digestion can be conducted. In general, the enclosure is sufficiently large to hold at least 50 bales in free liquid. For example, the depth of the enclosure, can vary anywhere from the height of one bale to the height of up to 7 bales or more (e.g., depending on the bale size). In one embodiment, the enclosure has a depth (i.e., distance between highest possible water level and lowest possible water level) between about 1 meter and about 25 meters, or any level therebetween. In one embodiment, the enclosure has a depth between about 2.5 meters and about 20 meters, between about 3 meters and about 15 meters, between about 5 meters and about 15 meters, or between about 6 meters and about 10 meters. Providing an enclosure having a depth of at least about 5 meters and less than about 15 meters may increase the possible scale of the process, may promote anaerobic conditions for the digestion, may facilitate flow in a continuous mode operation, may reduce problems associated with lack of stirring (i.e., when there is no stirring), may facilitate stacking of the bales (i.e., when stacked), and/or may promote submersion of the bales in the liquor.

Advantageously, the anaerobic digestion of the bales can be conducted on a large scale. In one embodiment, the enclosure can hold at least about 2,500 $m^3$, at least about 5,000 $m^3$, at least about 10,000 $m^3$, at least about 50,000 $m^3$, at least about 75,000 $m^3$, at least about 100,000 $m^3$, at least about 120,000 $m^3$, at least about 140,000 $m^3$, at least about 150,000 $m^3$, at least about 175,000 $m^3$, or at least about 200,000 $m^3$ of liquid. In one embodiment, the enclosure has a width of at least about 20 m, at least about 30 m, at least about 40 m, or at least about 50 m, and a length of at least about 60 m, at least about 80 m, at least about 100 m, at least about 125 m, at least about 150 m, at least about 175 m, at least about 200 m, at least about 250 m, or at least about 300 m. In one embodiment, the anaerobic digestion is conducted in continuous mode and the enclosure has a depth of about 8 m, a width of about 50 meters, and a length of about 350 meters. In one embodiment, the anaerobic digestion is conducted in batch mode and the enclosure has a depth between about 4-8 m, a width between about 40-70 m, and a length between about 100-200 m. When the enclosure has sloped wall (e.g., berms), the length and width are measured at ½ the depth of liquid. In one embodiment, in operation, the enclosure has a surface area between about 2000 $m^2$ and about 20,000 $m^2$, about 4000 $m^2$ and about 15000 $m^2$, about 6000 $m^2$ and about 10000 $m^2$, or about 2000 $m^2$ and 8000 $m^2$.

In terms of the shape and dimensions of the enclosure, a rectangular enclosure having a length to width ratio less than about 3:1 may be advantageous for batch processes, whereas a rectangular enclosure having a length to width ratio of at least about 4:1, or more likely at least 5:1, may be advantageous for continuous processes. For example, in one embodiment, the anaerobic digestion is conducted in continuous mode and the enclosure is a rectangular enclosure having a length to width ratio of at least about 7:1, at least about 8:1, or at least about 9:1. A length to width ratio of at least about 5:1 may facilitate plug flow. It can be advantageous to provide rectangular shaped enclosures having rounded corners (e.g., to prevent dead spots in the flow and/or sediment build up). In one embodiment, the anaerobic digestion is conducted in continuous mode (e.g., continuous plug flow) and the enclosure is a rectangular enclosure having a length to width ratio of about 2:1, 3:1, 4:1, 5:1, 6:1, 7:1, 8:1, 9:1, 10:1, or 11:1. In one embodiment, the anaerobic digestion is conducted in continuous mode (e.g., continuous plug flow) and the enclosure is a round enclosure.

In one embodiment, the enclosure is partitioned to provide multiple sections. Such partitions may be configured to prevent liquid from moving between sections (e.g., a dike) or may allow liquid to move between sections. Partitions that enable liquid flow between sections, but prevent bales from moving between sections, may be advantageous for anaerobic digestions conducted in continuous mode.

Each enclosure may or may not be provided with stirring/agitation. One advantage of certain embodiments of process(es)/system(s) disclosed herein related to the anerobic digestion of bales of cellulosic biomass is that mechanical mixing of the cellulosic biomass is not required, particularly for the early stages of the anaerobic digestion. In one embodiment, no mechanical mixing and/or agitation is provided throughout the anaerobic digestion. In one embodiment, mechanical mixing is not provided during the early stages of the anaerobic digestion, but is provided in a later stage of the anaerobic digestion (e.g., near the end of the channel in a continuous process). In one embodiment, jet mixers, which operate by pulling contents (e.g., digestate) from the digester and reintroducing them back into the digester (e.g., at high speed) via a motive pump, are used to provide some mixing of at least the liquid component. In one embodiment, gas mixers, which compress digester biogas and reintroduce the biogas back into the tank bottom thereby creating bubbles, are used to provide some mixing of at least the liquid component.

In general, one or more of the anaerobic digesters can be equipped with a slurry removal system (e.g., pipe, pump, etc.) to remove digestate from the enclosure. The slurry removal system can simply remove the digestate or can remove and process the digestate. For example, such processing can include a solids liquid separation, which provides a solid digestate stream and a liquid digestate stream. Pumping the digestate to a screw press is particularly advantageous as it may provide a solids stream having a consistency that facilitates further processing and/or direct application as a fertilizer and/or soil amendment and a liquid stream that is suitable for use as a fertilizer or inoculum. It can be particularly advantageous to recuperate at least part of the digestate from each digestion for use as inoculum (e.g., in another digestion). When digestate is used to inoculate the contents of the enclosure, the inoculum can include any part of the digestate including the liquid and/or solids. In one embodiment, a liquid fraction of the digestate is provided as inoculum. In one embodiment, a solid fraction of the digestate is provided as inoculum. In one embodiment, dewatered solids from a digestate removed from the enclosure are diluted and stored for use as inoculum for a new batch of bales. In one embodiment, the digestate is treated prior to being provided as inoculum. Alternatively, or additionally, each enclosure can include an access ramp, access door, or sloped walls configured to allow a front end loader to enter the enclosure and remove solid digestate. When the bale binding material is biodegradable and digested, the digestate may be processed without having to remove the binding material. However, when the bale binding material is not digested, binding removal may be provided. Depending on the slurry removal system, the binding for the bales can be separated from the digestate within the enclosure or after the digestate is removed from the enclosure. For example, in one embodiment, a binding removal system is provided downstream of anaerobic digestion to remove binding material from the digestate so that it does not interfere with downstream processing and/or use (e.g., a solids liquid separation). In one embodiment, the bales are secured with wire or twine and the binding removal system pulls the binding out of the digestate and/or filters the digestate. In one embodiment, the bales are secured with a plastic ribbon that floats, and the binding is removed by collecting it from the surface of the digestate.

In general, each anaerobic digester includes a cover, which can seal the enclosure (e.g., to prevent air from entering the digester and biogas from escaping to the atmosphere) and/or facilitate the collection of biogas. The covers may or may not be removable. For example, the cover may be a fixed roof, a floating cover, and/or a gas holding cover. While a fixed roof cover, which for example can be a hard flat or dome shaped roof fixed to the top of the enclosure, is possible, it may not be ideal when the enclosure spans a relatively large area. Floating covers can be rigid (e.g., a metal roof structure that floats on the digester contents and moves up and down via vertical guide members) or flexible (e.g., a flexible geomembrane). Flexible floating covers, which can rest on the surface of the digester contents, may be advantageous as they may provide submergence of any floating bales, can be configured with a gas collection system (e.g., where the biogas is removed at perimeter piping), and/or may be relatively economical for digesters that span a relatively large area (e.g., like lagoons). Flexible geomembrane covers can also be taut like a trampoline. Gas holding covers, which for example can be dual membrane covers or gas bladders, are often inflatable. For example, in a dual membrane cover, the outer membrane often remains inflated, while the inner membrane inflates and deflates in proportion to the biogas production, and thus may be suitable for pressurized applications. In one embodiment, a single type of cover is used to seal the enclosure (e.g., a flexible floating cover such a geomembrane cover). In one embodiment, more than one type of cover is used to seal the enclosure (e.g., a relatively inexpensive flexible floating cover can be used to seal part of an elongated enclosure and a dual membrane cover can be used to seal another part of the enclosure. When the enclosure is partitioned, a cover can be provided for each section or a single cover can seal multiple sections. In one embodiment, the cover is a removable cover (e.g., a removable floating cover or gas holding cover). Using a removable cover may facilitate loading bales of cellulosic biomass into the enclosure. The construction and the use of enclosures used for anaerobic digestion and/or the corresponding covers are known to those skilled in the art. In each case, the cover can be configured to collect biogas or facilitate the collection of biogas. Biogas can be used as a fuel to produce heat and/or power (e.g., after a cleaning process) or can be upgraded.

Biogas Upgrading

The term "biogas upgrading", as used herein, refers to a process where biogas (e.g., raw or cleaned biogas) is treated to remove one or more components (e.g., $CO_2$, $N_2$, $H_2O$, $H_2S$, $O_2$, $NH_3$, VOCs, and/or particulates), wherein the treatment increases the calorific value of the biogas. For example, biogas upgrading typically includes removing $CO_2$ and/or $N_2$ Biogas upgrading, which can include biogas cleaning, can produce an upgraded biogas that is a partially purified biogas (e.g., that requires further treatment in order to meet applicable specifications) or renewable natural gas (RNG).

The term "renewable natural gas" or "RNG", as used herein, refers to biogas that has been upgraded to meet or exceed applicable natural gas pipeline specifications, meet or exceed applicable quality specifications for vehicle use (e.g., CNG specifications), and/or natural gas withdrawn from a natural gas distribution system that is associated with the environmental attributes of upgraded biogas injected into the natural gas distribution system (e.g., a gas that qualifies as RNG under applicable regulations). Pipeline specifications include specifications required for upgraded biogas for injection into a natural gas distribution system. Pipeline quality standards or specifications may vary by region and/or country in terms of value and units. For example, pipelines standards may require the RNG to have a $CH_4$ level that is at least 95% or have a heating value of at least 950 BTU/scf. The percentages used to quantify gas composition and/or a specific gas content, as used herein, are expressed as mol %, unless otherwise specified. More specifically, they are expressed by mole fraction at standard temperature and pressure (STP), which is equivalent to volume fraction.

Biogas upgrading can be conducted using any suitable technology or combination of technologies that can separate $CH_4$ from one or more non-methane components in the biogas (e.g., $CO_2$, $N_2$, $H_2S$, $H_2O$, $NH_3$, $O_2$, VOCs, and/or particulates). For example, biogas upgrading technologies are often based on absorption, adsorption, membrane separation, and/or cryogenic separation. As will be understood by those skilled in the art, the technology used for the biogas upgrading can be dependent up the composition of the biogas and the desired purity of the upgraded biogas.

As biogas typically has a significant $CO_2$ content, biogas upgrading is often conducted in a biogas upgrading unit that includes at least one system for separating $CH_4$ from $CO_2$. Some examples of technologies that can remove $CO_2$ from biogas include, but are not limited to, absorption (e.g., water scrubbing, organic physical scrubbing, chemical scrubbing), adsorption (e.g., pressure swing adsorption (PSA)), membrane separation (e.g., $CO_2$ selective membranes based on polyimide, polysulfone, cellulose acetate, polydimethylsiloxane), and cryogenic separation. While some $CO_2$ removal systems may remove one or more other non-methane components in addition to $CO_2$ (e.g., $N_2$, $H_2S$, $H_2O$, $NH_3$, $O_2$, VOCs, and/or particulates), biogas upgrading units often include one or more other systems (e.g., dehydration units, $H_2S$ removal units, $N_2$ rejection units, etc.). For example, some $CO_2$ removal systems require that the biogas be cleaned upstream of $CO_2$ removal (e.g., remove impurities that can negatively affect the $CO_2$ removal unit). Alternatively, or additionally, the biogas can be cleaned and/or upgraded downstream of $CO_2$ removal. In general, the non-methane components can be removed by any combination of chemical and/or physical technologies, in one or more stages. For example, $H_2O$ may be removed using a standard biogas dehumidifier, whereas $H_2S$ may be removed using a commercial $H_2S$ removal unit (e.g., based on activated carbon, molecular sieve, iron sponge, water scrubbing, NaOH washing, and/or biofilter or biotrickling filter technologies). In some cases, one stage may remove more than one non-methane component. For example, in some cases, some $H_2S$ may also be removed during the water removal step.

The biogas upgrading can be conducted close to the anaerobic digester (e.g., at the same farm) or can be conducted at a centralized biogas plant (e.g., which receives raw, cleaned, or partially purified biogas from multiple sources). In one embodiment, the biogas produced from the anaerobic digestion is upgraded in one or more stages to provide upgraded biogas. In one embodiment, the upgraded biogas is injected into a natural gas distribution system (e.g., a natural gas grid). In one embodiment, the upgraded biogas is RNG.

In one embodiment, the carbon dioxide produced from the anaerobic digestion is captured (e.g., from the biogas or a tail gas from the biogas upgrading) and provided for storage.

Carbon Capture and Storage

In certain embodiments, carbon-containing material derived from the cellulosic biomass is stored and/or is provided for storage as part of carbon capture and storage (CCS). In general, CCS refers to one or more processes wherein $CO_2$ is captured from the atmosphere, or captured from a process that otherwise would release it to the atmosphere, and wherein carbon from the captured $CO_2$ is stored in order to prevent and/or delay its release to the atmosphere. For example, CCS can include capturing $CO_2$ from biogas produced from the anaerobic digestion of the cellulosic biomass and storing the captured $CO_2$ in subsurface formations (e.g., in geologic formations), or CCS can include storing carbon as carbon-containing material derived from the cellulosic biomass (i.e., captured $CO_2$ from the atmosphere via photosynthesis).

Capture of the $CO_2$ generated during anaerobic digestion (e.g., from the biogas) can be conducted using any suitable technology or combination of technologies that can capture $CO_2$ from a gas mixture. Technology that may be suitable for capturing $CO_2$ from one or more other gas components in a gas mixture includes, but is not limited to, absorption, adsorption, membrane separation, and cryogenic separation. The $CO_2$ can be captured upstream of biogas upgrading, as part of biogas upgrading, and/or from a tail gas produced from biogas upgrading. For example, since biogas upgrading can inherently include steps where $CO_2$ is separated from $CH_4$, such steps can be part of the $CO_2$ capture process, or can facilitate the $CO_2$ capture process, thereby reducing capital and operating costs.

Storage of $CO_2$ captured from the biogas, or the equal quantity of carbon dioxide displaced physically by the captured carbon dioxide, can be conducted using any suitable technology or combination of technologies. For example, carbon storage technologies, which are well known in the art, can sequester $CO_2$ in geological formations (i.e., subsurface formations). Suitable geological formations, which can occur in onshore or offshore settings, are often configured such that $CO_2$ injected therein, is trapped. For example, some examples of geological formations that may be suitable include saline aquifers, oil and natural gas reservoirs, unmineable coal seams, organic-rich shales, and/or basalt formations.

Storage of the captured $CO_2$, or the equal quantity of $CO_2$ displaced physically by the captured $CO_2$, can also be part of carbon capture, utilization, and storage, or CCUS. CCUS technologies encompass the use of the captured $CO_2$. For example, CCUS can include using the captured $CO_2$, or an equal quantity of $CO_2$ displaced by the captured carbon dioxide, for enhanced oil recovery (EOR). CCUS technologies may include the use of the captured $CO_2$, or an equal quantity of $CO_2$ displaced physically by the captured $CO_2$, for producing a product (e.g., the carbon can be stored within the product). Such products may include building materials such as cement, concrete, or aggregates, chemicals, fuels, and/or food and beverages. The term "CCS", as used herein, can refer to CCS and/or CCUS.

As will be understood by those skilled in the art, it can be advantageous for the captured $CO_2$, or an equal quantity of $CO_2$ displaced by the $CO_2$, to be stored using a method recognized by the applicable regulatory authority for reducing lifecycle GHG emissions and/or mitigating climate change. For example, some regulations may require substantially permanent sequestration of the captured $CO_2$ and/or sequestration with a maximum leakage rate (e.g., monitoring of carbon dioxide leakage from storage for a certain time period may be mandatory). Some regulations may require the use of the captured $CO_2$ to displace the use of an equal quantity of fossil based carbon dioxide located in a subsurface formation.

Appropriate storage of the $CO_2$ can reduce GHG emissions and/or mitigate climate change (e.g., can reduce the carbon intensity and/or lifecycle GHG emissions of the fuel, chemical, and/or product produced from the process, relative to no CCS). The level of GHG reduction achieved may be dependent on whether it is all biogenic, the applicable regulatory authority, the permanence of the storage, and/or whether its use displaces the use of fossil fuel products. In one embodiment, the captured $CO_2$ is sequestered in at least one geological formation. For example, in one embodiment the captured $CO_2$ is sequestered in a saline aquifer or is sequestered in an oil/natural gas reservoir as part of enhanced oil recovery (EOR). In one embodiment, the captured $CO_2$ is stored in concrete. In one embodiment, storage of the captured $CO_2$ from one or more of the biogases permanently displaces fossil based $CO_2$ emissions.

Alternatively, or additionally, appropriate storage of carbon containing material derived from the cellulosic biomass can reduce GHG emissions and/or mitigate climate change (e.g., can reduce the carbon intensity and/or lifecycle GHG emissions of the fuel, chemical, and/or product produced from the process, relative to no CCS). In certain embodiments, carbon-containing material obtained or derived from the digestate from anaerobic digestion is provided for storage as part of CCS, or for use as a by-product of the process, thereby reducing the carbon intensity and/or GHG emissions of the fuel, chemical, or product produced from the process. In certain embodiments, this includes processing the digestate (e.g., the digestate is treated prior to CCS). For example, digestate can be subjected to a hydrothermal liquefaction to provide a bio-oil that can be used as a fuel or sequestered and/or char. Char, which is biologically unavailable, can be provided as a soil amendment where it can store the carbon in the soil for centuries. In some cases, the sequestration method is selected to prevent biodegradation of the material and/or trap GHGs in the event of biodegradation. In some cases, the material is treated in a process to reduce the potential for biodegradation.

Advantageously, providing CCS of carbon-containing material derived from part of the biomass not converted to fuel, chemical, or product, can result in so-called negative emissions. For example, consider the $CO_2$ produced from the anaerobic digestion of biomass. The release of this $CO_2$, which is biogenic, to the atmosphere simply returns to the atmosphere carbon that was recently fixed by photosynthesis. That is, biogenic $CO_2$ is generally considered to be carbon neutral (e.g., its release does not result in an increase in net GHG emissions). However, if biogenic $CO_2$ is instead captured and stored so as to release or delay its release to the atmosphere, then there can be a net transfer of $CO_2$ from the atmosphere to storage (e.g., so called negative emissions).

Negative emissions can be the basis for BECCS, which stands for bioenergy with carbon capture and storage. For example, in some cases, BECCS, which is a group of technologies that combine extracting bioenergy from biomass with CCS, can be viewed as a process where biomass (e.g., plants) is used to extract $CO_2$ from the atmosphere, the biomass is processed to produce bioenergy (e.g., heat, electricity, fuels) while releasing $CO_2$, and the $CO_2$ produced during the processing is captured and stored such that there is a transfer of $CO_2$ from the atmosphere to storage. BECCS is increasing discussed as a means to decrease $CO_2$ emissions and/or $CO_2$ concentrations in the atmosphere.

Fuel, Chemical, or Product Production

In general, the process produces fuel, chemical, or product which can be raw biogas, upgraded biogas, and/or a fuel, chemical, or product produced from the raw or upgraded (e.g., hydrogen, methanol, gasoline, diesel, jet fuel, marine fuel, ammonia, fertilizer, etc.). For example, upgraded biogas and/or RNG can be subjected to methane reforming (e.g., steam methane reforming) to produce syngas. The syngas can be used to produce a fuel directly (e.g., Fischer Tropsch gasoline or diesel, jet fuel) or can be purified to produce hydrogen.

In one embodiment, the raw biogas, cleaned biogas, or upgraded biogas is used to produce hydrogen. When the hydrogen is derived from biogas it may be referred to as renewable hydrogen. Renewable hydrogen, which can be the fuel produced from the process, can be used as a fuel (e.g., transportation fuel) or can be used as an industrial feedstock to produce fuel (e.g., transportation fuel(s)), chemicals (e.g., ammonia), and/or products (e.g., fertilizer). For example, in one embodiment, the renewable hydrogen is used in the hydroprocessing (e.g., hydrocracking and/or hydrotreating) of crude-oil derived liquid hydrocarbon such that the renewable hydrogen is incorporated into a crude-oil derived liquid hydrocarbon to produce gasoline, diesel, and/or jet fuel having renewable content (e.g., see U.S. Pat. Nos. 8,658,026, 8,753,854, 8,945,373, 9,040,271, 10,093,540, 10,421,663, 10,723,621, and 10,981,784). The term "crude oil derived liquid hydrocarbon", as used herein, refers to any carbon-containing material obtained and/or derived from crude oil that is liquid at standard ambient temperature and pressure. The term "renewable content", as used herein, refers the portion of the fuel(s) that is recognized and/or qualifies as renewable (e.g., a biofuel) under applicable regulations. The quantification of the renewable content can be determined using any suitable method and is typically dependent upon the applicable regulations. Advantageously, such fuels can replace and/or be used with non-renewable gasoline, diesel, and/or jet fuel without affecting performance and/or operation (e.g., are drop-in fuels). Further advantageously, such fuels can be produced at existing oil refineries using existing equipment.

In one embodiment, the process produces renewable hydrogen from the upgraded biogas (e.g., from the steam methane reforming of RNG or the coprocessing of RNG and nonrenewable natural gas). In one embodiment, the renewable hydrogen is used in the hydroprocessing (e.g., hydrocracking and/or hydrotreating) of crude-oil derived liquid hydrocarbon to produce aviation fuel having renewable content. In one embodiment, the upgraded biogas is provided to a fuel production facility that produces hydrogen, wherein the hydrogen is used in the hydroprocessing (e.g., hydrocracking and/or hydrotreating) of crude-oil derived liquid hydrocarbon to produce aviation fuel having renewable content. These embodiments are particularly advantageous as it could help decarbonize commercial air travel and/or extend the life of older aircraft types by lowering their carbon footprint. In one embodiment, the renewable hydrogen is used in the hydroprocessing (e.g., hydrocracking and/or hydrotreating) of renewable fats and/or oils (e.g., algae, jatropha, tallows, camelina, pyrolysis oil produced from biomass, etc.) to produce renewable gasoline, diesel, and/or jet fuel. This embodiment is advantageous as the resulting fuel can be fully renewable and have a reduced carbon intensity (i.e., relative to an analogy process where the hydrogen is produced from fossil based natural gas).

Renewable hydrogen may play a role in decarbonization, where the economy either emits no GHG emissions or offsets its GHG emissions. Many countries have made commitments to reach net-zero carbon emissions by 2050. Renewable hydrogen is advantageous in terms of reducing carbon emissions because it can be used in or for many sectors that are considered hard-to-decarbonize, including long-haul trucking, shipping (marine), aviation, some district heating, and/or energy-intensive industries (e.g., steel, cement, oil refining, and ammonia production).

Alternatively, or additionally, fuel produced from the process can be derived from the digestate. For example, in one embodiment, the digestate removed from the anaerobic digestion is subjected to a solids/liquid separation and at least a portion of the solid fraction is subjected to a hydrothermal liquefication (HTL).

HTL is a thermal depolymerization process used to convert wet biomass and/or other macromolecules into crude-like oil under moderate temperature (e.g., between about 200° C. and about 400° C.) and high pressure (e.g., between about 5 MPa (or about 725 psig) and about 28 MPa (or about 4000 psig)). In addition to the crude-like oil, also referred to herein as bio-oil, HTL typically produces a solid residue, an aqueous phase, and gas. The solid residue can include char and/or inorganic salts. The aqueous phase can include organic and/or inorganic water solubles. Some value added chemicals that can be produced from HTL include phenolics, phenyls, and fatty acids.

HTL, which can be conducted in batch or continuous mode, is typically conducted in an oxygen limited environment (e.g., in a closed container pressurized using either an inert gas (e.g., nitrogen, helium, or argon) or a reducing gas (e.g., hydrogen)). As will be understood by those skilled in the art, the yield and/or quality of bio-oil, char, and/or value added chemicals produced from the HTL process can be dependent on the type of feedstock, the process conditions (e.g., the reaction temperature, pressure, reaction time, solids loading, and selection of catalyst and/or capping agent, if used), and/or the system used for the HTL process.

With regard to the reaction temperature, HTL is typically conducted at temperatures between about 250° C. and about 375° ° C., and often at temperatures between about 300° C. and about 370° ° C. (e.g., at about 350° C.). The pressure is often between about 10 MPa (or about 1450 psig) and 22 MPa (or about 3200 psig). The reaction temperature and pressure are often selected to facilitate depolymerization while maintaining a liquid phase and preventing formation of a supercritical fluid. With regard to reaction time, HTL can be conducted from anywhere from minutes to hours, but is often conducted for about 60 minutes or less, or more often about 30 minutes or less (e.g., from between 5 and 30 minutes). A portion of the reaction time is the hold time, which refers to the time that the feedstock is held at about the reaction temperature (e.g., does not including the heating up time and/or cooling down time). For example, for a batch process the hold time refers to the time that the reactor is maintained at the reaction temperature. It is possible for the hold time to be zero (e.g., cooling can begin once the reaction temperature has been reached). For a continuous process the reaction time can refer to the hydraulic or the solids retention time, which can be equal or different. It is also possible in a continuous system for the hold time to be zero (e.g., cooling can begin once the reaction temperature has been reached). The reaction time may be selected to produce a certain bio-oil, char, and/or value added chemical yield, and may be dependent upon the reaction temperature, heating rate(s), and/or whether catalysts are used. The heating rate, which refers to the rate of temperature increase per unit time, may also affect yields.

The solids loading, which is discussed herein in terms of the "solids consistency," is usually between about 5% and 40% dry solids, and often between about 10% and 28% dry solids. The term "solids consistency" or simply "consistency" refers to the amount of undissolved dry solids or "UDS" in a sample, and is often expressed as a ratio on a weight basis (wt:wt), or as a percent on a weight basis, for example, % (w/w), also denoted herein as wt. %. For example, consistency can be determined by filtering and washing the sample to remove dissolved solids and then drying the sample at a temperature and for a period of time that is sufficient to remove solvent (water) from the sample, but does not result in thermal degradation of the sample, thereby providing dry solids. The consistency is the weight of the dry solids divided by the weight of the sample. Lower consistencies generally provide sufficient water to support the hydrolysis of the feedstock, but may produce less bio-oil due to relatively low amounts of carbon and/or may be associated with excessive heating costs due to the high water content. At very high consistencies there may be insufficient water to support the hydrolysis of the feedstock and/or there may be challenges with pumping the materials.

With regard to catalysts, the use of homogeneous and/or heterogeneous catalysts can improve the quality of products and/or yields. For example, the use of alkali catalysts, such as potassium carbonate, may increase bio-oil yields and/or reduce char yields. Alkali catalysts are often used in HTL to increase the pH of the initial mixture to between 11-13. The use of capping agents (e.g., ethanol, phenol) may enhance the depolymerization process and/or may reduce char production. With regard to the system used for the HTL process, any suitable configuration and/or suitable process steps may be used. For example, the HTL process may be conducted as a batch process, and thus may include pressuring a suitable container (e.g., Parr type reactor) with inert gas to a relatively low pressure (e.g., about 150 psig), so that as the container is heated to the reaction temperature the pressure will increase to the desired pressure (e.g., 2900 psig). Alternatively, the HTL process can be conducted in a long pipe configured to function as a plug flow reactor, in conjunction with appropriate pumps, etc. (e.g., a continuous pipe reactor).

Depending upon the feedstock, process conditions, and/or system, the process may include one or more separation steps and/or extraction steps. For example, many HTL processes include solid-liquid separations and/or liquid-liquid separations (e.g., to separate the aqueous phase and bio-oil). As will be understood by those skilled in the art, one or more of these process parameters are often selected in dependence upon one or more other process parameters and/or in dependence upon the desired products and/or properties. For example, a higher temperature may be combined with a shorter reaction time. With regard to the desired properties, different conditions and/or systems can produce different bio-oils, which may for example differ in terms of molecular weight distribution, oxygen content, and/or heating values.

In certain embodiments of the disclosure, the feedstock for HTL contains at least part of the digestate from the anaerobic digestion of whole bales. For example, the solid fraction of the digestate, which may contain a significant lignin content, may be converted to bio-oil via HTL. Appropriate selection of the conditions for the HTL of one or more components of the digestate will be understood to those skilled in the art having the benefit of the teachings herein. For example, in one embodiment, the process includes producing a slurry containing the solid fraction having a pH of about 12 (e.g., by adding suitable alkali such as sodium hydroxide, sodium carbonate, calcium hydroxide, calcium carbonate, potassium hydroxide, potassium carbonate, or a mixture thereof) and subjecting the slurry to HTL by heating the slurry to 300° C. to 350° C. for about one hour. After cooling to ambient temperature, the resulting slurry may contain bio-oil in the top layer, then the aqueous layer that is rich in alkali, and solids (e.g., char) at the bottom (e.g., for batch processes). The three layers are separated (e.g., by gravity settling). The bio-oil may be used directly (e.g., in heavy engines, including marine and rail) or can be processed (e.g., hydroprocessed) to produce a transportation fuel (e.g., diesel, gasoline, jet fuels, marine, or rail).

In general, the bio-oil can be processed (e.g., upgraded) using any suitable technology, or combination of technologies, to produce one or more fuels (e.g., transportation fuels) and/or value added chemicals. For example, such processing can include technology that is often used for upgrading petroleum-based oils (e.g., cracking or hydroprocessing). For example, bio-oil can be upgraded via a hydroprocessing process selected to remove oxygen and/or increase saturation. Such hydroprocessing typically includes catalytic hydrogenation wherein the bio-oil is contacted with a heterogeneous catalyst (e.g., containing metal such as Co—Mo, Ni—Mo, Pd, Ni, Ru, and the like, such as $CoMo/Al_2O_3$) in the presence of hydrogen and may be conducted at elevated temperatures (e.g., between about 300° C. and about 700° C., such as about 550° C.) and pressures (e.g., between about 1500 psig and about 4400 psig). Alternatively, the bio-oil can be subjected to catalytic cracking, which uses a heterogeneous catalyst (e.g., a zeolite catalyst such as ZSM-5 and the like), but does not require hydrogen. The bio-oil may be processed alone or may be co-processed with a petroleum-based oil (e.g., depending on the quality of the bio-oil). Alternatively, or in addition to hydroprocessing (e.g., hydrodeoxygenation) or catalytic cracking, the bio-oil upgrading may include filtration (e.g., hot vapor filtration), solvent extraction, emulsification, esterification, and/or steam reforming. With regard to the latter, subjecting the bio-oil to steam reforming can produce hydrogen, which can be used as a fuel or as an industrial feedstock to produce fuel, chemical, or product. Appropriate selection of the conditions for upgrading bio-oil will be understood to those skilled in the art having the benefit of the teachings herein. In one embodiment, the bio-oil is used to produce marine fuel. In one embodiment, the bio-oil is used to produce aviation fuel. In one embodiment, the bio-oil is used to produce long-haul trucking fuel.

While it can be advantageous to use the digestate from the anaerobic digestion of baled cellulosic biomass as feed for HTL, it can also be advantageous to use the digestate from the anaerobic digestion of unbaled cellulosic biomass, and in particular of unbaled agricultural residues such as straw, as feed for HTL (e.g., even when subjected to size reduction). For example, while a significant amount of hemicellulose and cellulose in agricultural residues can be converted to biogas, there may remain a significant amount of cellulose and/or lignin that is not digested, but that can be converted to additional fuel via the HTL process. Moreover, HTL, which can be used to treat materials with high moisture content, may be particularly suitable for digestate as it can produce one or more products without requiring extensive drying of the digestate.

In certain embodiments of the disclosure, an agricultural residue (e.g., baled or milled straw) is subjected to anaerobic digestion and at least a portion of the digestate produced therefrom is subjected to hydrothermal liquefaction to produce bio-oil and/or char. Notably, this process is quite different and includes various synergistic advantages relative to a process where the feedstock is pretreated via HTL for the purpose of improving anaerobic digestion (e.g., using HTL to destroy the internal structure of straw in order to release more carbohydrate). For example, the portion of the feedstock that is readily converted to methane can be converted in this first step, while the more challenging to digest portion of the feedstock is subsequently processed via HTL to produce fuel. In addition to reducing the volume of material fed into the more energy intensive HTL, the material (e.g., digestate) may be more readily transferred (e.g., pumped) than undigested straw feedstock. Using straw as a feedstock for the anaerobic digestion followed by HTL process offers various synergistic advantages over other feedstocks such as manure. For example, since straw can contain a significant amount of hard-to-digest lignin, the digestate from anaerobic digestion can contain a significant amount of lignin in addition to any unconverted cellulose/hemicellulose (e.g., protected by lignin). Accordingly, the residue from anaerobic digestion of straw can be a good feedstock for HTL. Alternatively, or additionally, the bio-oil and/or char can be provided for use in CCS. In general, the carbon intensity of the fuel produced and/or the lifecycle GHG emissions of the fuel, chemical, or product, can be relatively low when the feedstock is an agricultural residue or energy crop and/or when CCS is used (e.g., to capture and sequester the $CO_2$ generated during the anaerobic digestion). The term “carbon intensity” or “CI” refers to the quantity of lifecycle GHG emissions, per unit of fuel energy, and is often expressed in grams of $CO_2$ equivalent emissions per unit of fuel (e.g., $gCO_2e/MJ$ or $gCO_2e/MMBTU$). As will be understood by those skilled in the art, CI and/or lifecycle GHG emissions are typically determined using Lifecycle Analysis (LCA), which identifies and estimates all GHG emissions in producing a fuel, from the growing or extraction of raw materials, to the production of the fuel, chemical and/or product, through to the end use (e.g., well-to-wheel). Those skilled in the art will understand that CI and/or lifecycle GHG emission values for a given fuel, chemical, and/or product can be dependent upon the methodology and/or LCA model used (e.g., as required by the applicable regulatory authority). The CI values recited herein are determined using the CA-GREET model (e.g., see, https://ww2.arb.ca.gov/resources/documents/lcfs-life-cycle-analysis-models-and-documentation), unless otherwise specified. As the fuel, chemical, or product is produced at least in part using cellulosic biomass and/or has a relatively low CI and/or lifecycle GHG emissions, one or more credits (e.g., fuel credits) can be generated.

Fuel credits are used to incentivize renewable fuels, often in the transportation sector. For example, fuel credits can be used to demonstrate compliance with some government initiative, standard, and/or program, where the goal is to reduce GHG emissions (e.g., reduce CI in transportation fuels as compared to some baseline level related to conventional petroleum fuels) and/or produce a certain amount of biofuel (e.g., produce a mandated volume or a certain percentage of biofuels). The target GHG reductions and/or target biofuel amounts may be set per year or for a given target date. Some non-limiting examples of such initiatives, standards, and/or programs include the Renewable Fuel Standard Program (RFS2) in the United States, the Renewable Energy Directive (RED II) in Europe, the Fuel Quality Directive in Europe, the Renewable Transport Fuel Obligation (RTFO) in the United Kingdom, and/or the Low Carbon Fuel Standards (LCFS) in California, Oregon, or British Columbia).

The term "fuel credit", as used herein, refers to any rights, credits, revenues, offsets, GHG gas rights, or similar rights related to carbon credits, rights to any GHG gas emission reductions, carbon-related credits or equivalent arising from emission reduction trading or any quantifiable benefits (including recognition, award or allocation of credits, allowances, permits or other tangible rights), whether created from or through a governmental authority, a private contract, or otherwise. A fuel credit can be a certificate, record, serial number or guarantee, in any form, including electronic, which evidences production of a quantity of fuel meeting certain life cycle GHG emission reductions relative to a baseline (e.g., a gasoline baseline) set by a government authority. Non-limiting examples of fuel credits include RINs and LCFS credits. A Renewable Identification Number (or RIN), which is a certificate that acts as a tradable currency for managing compliance under the RFS2, may be generated for each gallon of biofuel (e.g., ethanol, biodiesel, etc.) produced. A Low Carbon Fuel Standard (LCFS) credit, which is a certificate which acts as a tradable currency for managing compliance under California's LCFS, may be generated for each metric ton (MT) of $CO_2$ reduced.

In general, the requirements for generating or causing the generation of credits (e.g., fuel credits) can vary by country, the agency, and or the prevailing regulations in/under which the fuel credit is generated. In many cases, fuel credit generation may be dependent upon a compliance pathway (e.g., predetermined or applied for) and/or the biofuel meeting a predetermined GHG emission threshold. For example, with regard to the former, the RFS2 categorizes biofuel as cellulosic biofuel, advanced biofuel, renewable biofuel, and biomass-based diesel. With regard to the latter, to be a renewable biofuel under the RFS2, corn ethanol should have lifecycle GHG emissions at least 20% lower than an energy-equivalent quantity of gasoline (e.g., 20% lower than the 2005 EPA average gasoline baseline of 93.08 $gCO_2e/MJ$). In low carbon-related fuel standards, biofuels may be credited according to the carbon reductions of their pathway. For example, under California's LCFS, each biofuel is given a CI score indicating their GHG emissions as grams of $CO_2$ equivalent per megajoule (MJ) of fuel, and fuel credits are generated based on a comparison of their emissions reductions to a target or standard that may decrease each year (e.g., in 2019, ethanol was compared to the gasoline average CI of 93.23 $gCO_2e/MJ$), where lower CIs generate proportionally more credits.

Example 1

Figure 2:
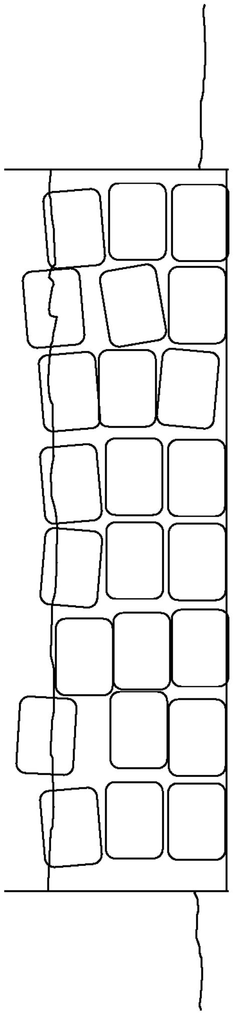
FIG. 2 is a schematic diagram of an enclosure containing a plurality of bales of cellulosic biomass.
Figure 3:
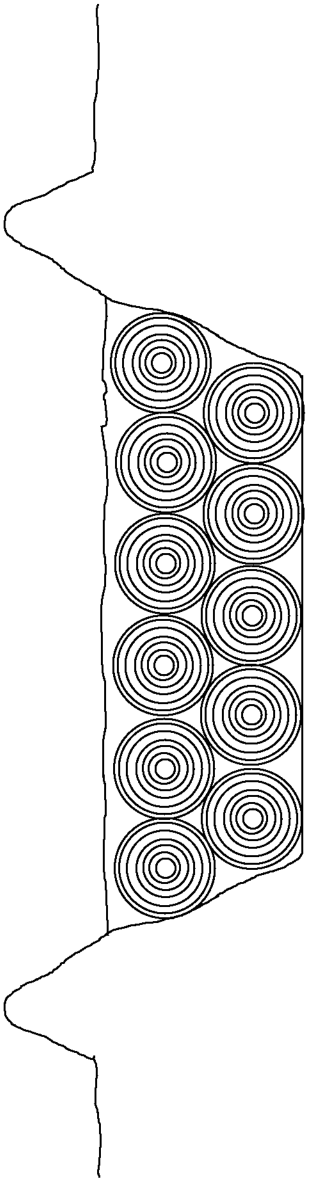
FIG. 3 is a schematic diagram of another enclosure containing a plurality of bales of cellulosic biomass.

In the following prophetic example wheat straw is baled in the field (e.g., multiple fields) and transported to one or more anaerobic digesters. Each bale is approximately 3×4×8 feet, has a moisture content of about 15%, and weighs about 420 kg (i.e., a density of about 154 $kg/m^3$). Each of the anaerobic digesters is an elongated earthen basin that is approximately 8 meters deep (4 meters of which is below grade), 50 meters wide, and 350 meters long (i.e., a volume of about 140,000 $m^3$). The bales are soaked in water, drained, injected with inoculum, and loaded into one of the anaerobic digesters. More specifically, the bales are loaded into the digester to provide up to about 8 layers of bales. The bales may be stacked one upon the other as illustrated in FIG. 2 (e.g., relatively closely packed) or can be stacked in a brick pattern with space between adjacent bales (e.g., to provide interstitial areas between bales as illustrated in FIG. 3 for round bales). The digester is filled with water and more inoculum. The number of bales within the digester may, for example, be about 25,000, which has been calculated to correspond to an initial solids consistency of 6.4% (w/w). Some of the bales float, some rest on the bottom. The digester is sealed to substantially prevent oxygen from entering the digester and/or prevent biogas from escaping. The bales move through the digester at a rate selected such that, after start-up, each newly added bale takes 40-60 days to move the digester (e.g., 350 meters).

Figure 5:
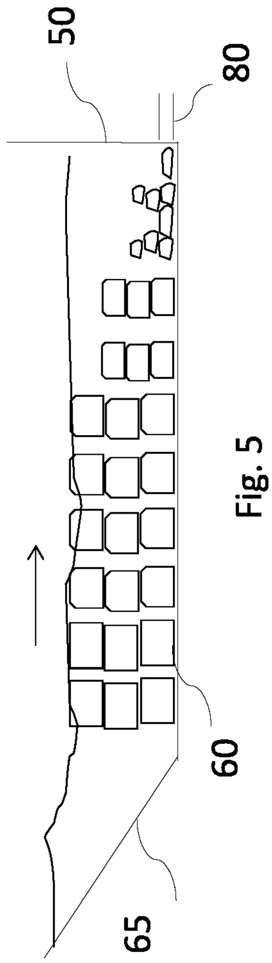
FIG. 5 is a cross sectional side view of the elongated enclosure shown in FIG. 4.
Figure 6:
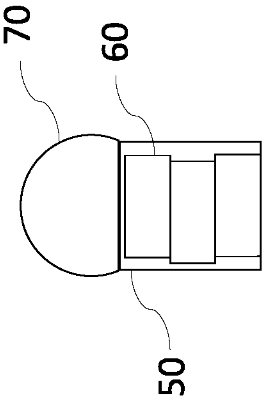
FIG. 6 is a cross sectional end view of the elongated enclosure shown in FIG. 4.
Figure 4:
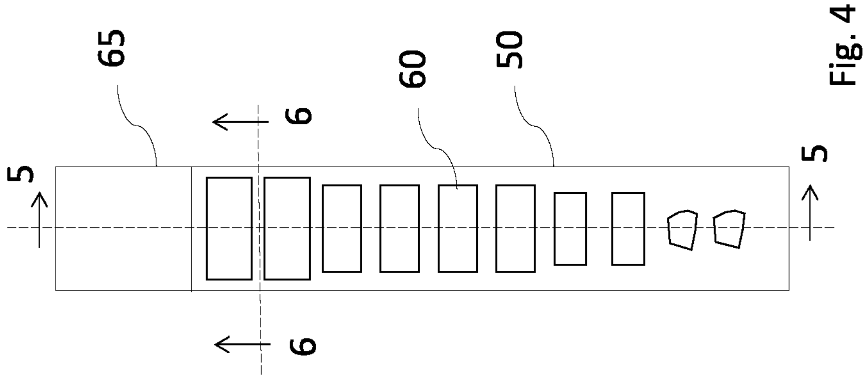
FIG. 4 is top view of an elongated enclosure containing a plurality of bales of cellulosic biomass.

Referring to FIGS. 4, 5, and 6, the elongated enclosure 50 includes an access ramp 65 that allows vehicles to enter the enclosure to facilitate loading the bales. Once the bales are loaded and liquid is added, the bales 60 move through the elongated enclosure 50 (from the top to the bottom of FIG. 4), as the cellulosic biomass is digested. Early in the anaerobic digestion the bales will remain intact. As the cellulosic biomass is digested the bales may lose their shape. By the time the cellulosic biomass reaches the end of the digester, wherein it is removed as digestate via pipe 80, it may no longer resemble a bale. The biogas is captured in a dual membrane cover 70 that extends along at least part of the digester. This system processes 375 tonnes of straw per day.

Advantageously, this relatively high processing rate is achieved without stirring and/or without using steel walled digesters. One advantage of subjecting bales of cellulosic biomass to an anaerobic digestion is that it can scale up well and is suitable for large scale projects. In one embodiment, the project is a commercial scale project. For example, in one embodiment, it produces more than 3,400 million BTU energy from biogas per day. Another advantage is that it may be more stable and/or may provide a more continuous operation (e.g., with fewer shut downs related to imbalances in pH, temperature, salinity, toxins, etc.). In particular, there may be various advantages related to the operating conditions. For example, the contents of the anaerobic digester may not need to be heated because heat generated within the bales may heat up the liquid (e.g., cooling may even be required). In addition, cellulosic biomass from crops may have a significant inorganic content (e.g., a relatively high $K^+$, $Na^+$, $Ca^{2+}$, $Mg^{2+}$ content). In particular, energy crops and/or agricultural residues may contain significant amounts of potassium carbonate ($K_2CO_3$), calcium carbonate ($CaCO_3$), and/or sodium carbonate ($Na_2CO_3$). These soluble salts, which may be referred to as "alkali inherent to the biomass" or "inherent alkali" as they can consume acid, can provide a buffering effect. Accordingly, they may help maintain the pH within the desired range. This effect is less likely to be observed for the anaerobic digestion of loose straw as some of the soluble salts may be removed during the processing of the loose straw for anaerobic digestion. In addition, cellulosic biomass can have a relatively high C/N ratio (e.g., around 50 for corn stover), which is often outside the optimum range for anaerobic digestion. Accordingly, loose cellulosic biomass such as straw is often co-digested with manure in order adjust the C/N ratio. However, in some of the process(s)/system(s) disclosed herein, a large amount of digestate is added to facilitate the anaerobic digestion of the bales. This digestate can have a relatively low C/N ratio, which can reduce the C/N ratio of the anaerobic digester contents. Some of the digestate can also be applied to land (e.g., as a fertilizer and/or soil amendment).

Example 2

The following samples were prepared for anaerobic digestion. Sample 1 contained straw stalks that were ground using a Wiley Mill to pass a 20-mesh sieve (labelled ground stalks in FIG. 7). Sample 2 contained straw stalks that were cut with scissors into pieces having a length between about 0.75 inches and about 1 inch (labelled short stalks in FIG. 7). Sample 3 contained straw stalks that were cut with scissors into pieces having a length of about 2.75 inches (labelled long stalks in FIG. 7). Sample 4 contained straw stalks that were cut with scissors into pieces having a length of about 2.75 inches, which were then bundled to a bulk density of about 140 $kg/cm^3$ (labelled bundled stalks in FIG. 7).

In each case, the straw was mixed with water, nutrient media, and inoculum. More specifically, inoculum was added to provide an inoculum substrate ratio (ISR) of 2:1, where the ISR is determined on a volatile solids (VS) basis (e.g., inoculum VS to substrate $VS_{dig}$, where $VS_{dig}$ refers to the digestible portion of the volatile solids). The amount of water, nutrient media, and inoculum added resulted in total solids of 1% (e.g., from the straw, not inoculum or nutrient media). The inoculum was obtained from an anaerobic digester fed dairy manure, mixed agricultural residues, and local factory organic residues. The anerobic digestion was conducted in an unmixed 500 ml bottle held at 37° (water bath). The biomethane potential (BMP) was analyzed by measuring methane produced using an AMPTS II from Bioprocess control. The methane production from each digestion is illustrated in FIG. 7.

Figure 7:
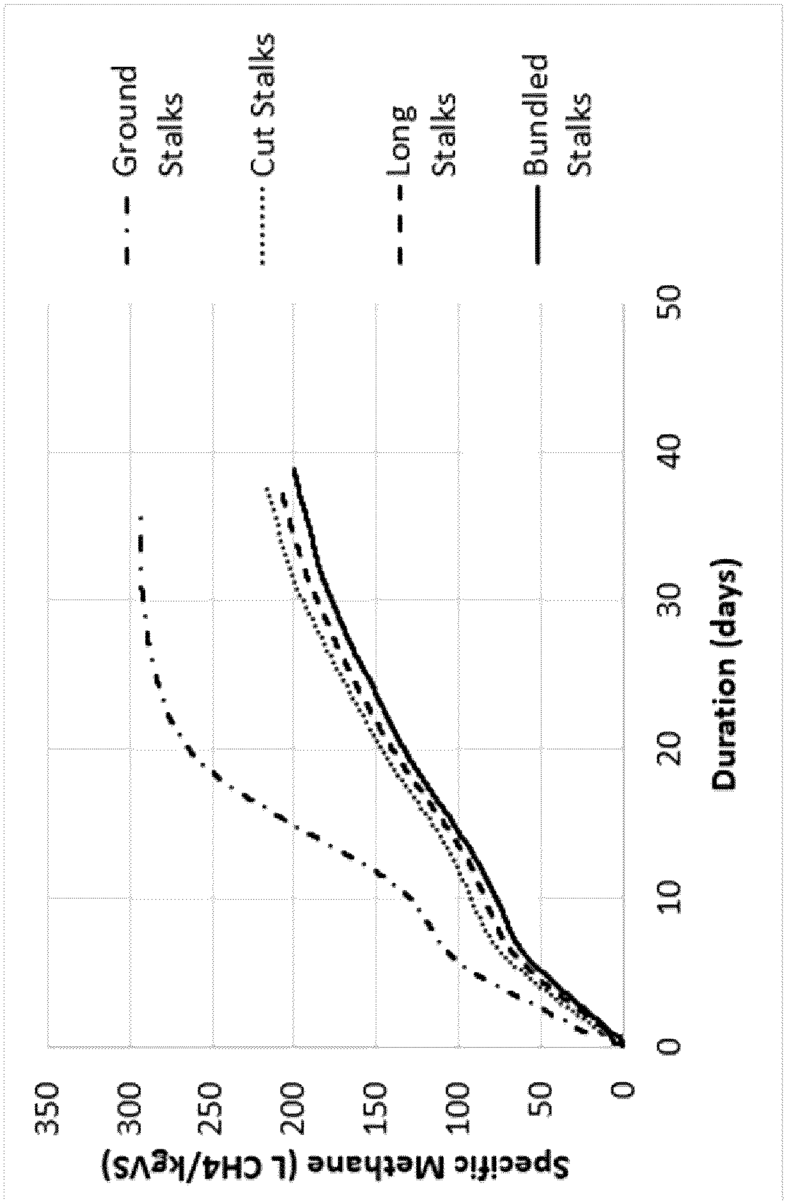
FIG. 7 is a plot showing methane produced as a function of time for the anaerobic digestion of straw stalks.

Referring to FIG. 7, while grinding the stalks to 20 mesh facilitated the production of more biogas (e.g., at least initially), a reasonable amount of methane is produced from the unground stalks. In addition, the difference in amount of methane produced from the different unground stalks (e.g., short, long, bundled stalks) is surprisingly minimal. These results demonstrate the potential for the use of bales of cellulosic material for anaerobic digestion.

Since less of the cellulosic biomass may be converted to biogas, the anaerobic digestion of bales of cellulosic material may be particularly advantageous when at least some of the solid digestate is subjected to HTL. For example, this can allow the portion of the feedstock that is readily digested to be converted to a first fuel/product (e.g., upgraded biogas, or a fuel/product derived therefrom) with reduced process energy and/or reduced cost, while at least a portion of the remaining feedstock is converted to a second fuel/product (e.g., bio-oil, or a fuel/product derived therefrom). Advantageously, the bio-oil yield may be relatively high as a result of the at least partial digestion of the straw. Further advantageously, the lifecycle GHG emissions associated with the first and/or second fuels may be relatively low (e.g., relative using only one of the anaerobic digestion or HTL processes) due to less waste (e.g., digestate), one or more CCS processes, less heat required for HTL due to smaller volumes, the production of one or more by-products, and/or thermal integration (e.g., between HTL and anaerobic digestion). In certain embodiments, at least a portion of the liquid from the HTL is recycled to the anaerobic digestion (e.g., directly or after processing), thereby reducing water usage, generating additional biogas, and/or providing salts and/or nutrients. For example, the liquid phase from the HTL may be rich in alkali. The alkali can be recovered from the aqueous liquid phase and used in either the HTL or the anaerobic digestion. The liquid phase can also include organic compounds. The aqueous organic waste can be recycle to anaerobic digestion or, with the char, can be burned as fuel.

In general, one advantage of certain above-described embodiments, is that the anaerobic digestion is conducted on bales of cellulosic biomass. Relative to other forms of biomass densification, such as pelleting and briquetting, baling biomass requires less processing and can be conducted in the field. In addition, subjecting whole or bifurcated bales of cellulosic biomass to an anaerobic digestion reduces costs and simplifies the process (e.g., relative to loose biomass). In certain above-described embodiments, the process may include providing no stirring throughout the anaerobic digestion, providing no pretreatment of the cellulosic material in advance of anaerobic digestion, providing a lined or unlined earthen basin as the anaerobic digester, conducting the anaerobic digestion as a continuous process, conducted the anaerobic digestion as a batch process, conducting the anaerobic digestion as a continuous plug flow anaerobic digestion, providing no on-site storage of the bales of cellulosic biomass (i.e., apart from within the enclosure), stacking the bales one on top of the other in close contact or to provide interstitial spaces, providing no external heating, providing cooling of the liquid (e.g., by withdrawing liquid and cooling it with a heat exchanger prior to reinjection), providing a dual membrane cover, providing a flexible cover that rests on the liquid within the enclosure, providing bales having a nominal volume of at least 50 L, not removing binding material for the anaerobic digestion, controlling the pH in the enclosure by adding and/or recycling a liquid fraction of a digestate (e.g., where the only base added is from the feedstock), adding free liquid into the enclosure in an amount such that the mass of free liquid is at least about 50% the mass of wet or dry bales of cellulosic biomass, conducting the anaerobic digestion at a solids consistency less than about 15 wt %, and/or adding aqueous liquid (e.g., before, during, and/or after the bales are loaded into the anaerobic digester) such that the height of the liquid level when the bales are in the enclosure is at least 30 cm, at least 40 cm, at least 50 cm, at least 60 cm, at least 70 cm, at least 80 cm, at least 90 cm, or at least 1 meter greater than a height of one of the bales.

Advantageously, combining the anaerobic digestion of bales of cellulosic material with a downstream HTL obviates various challenges associated with the conventional anaerobic digestion of cellulosic material, including, i) pretreatment of the cellulosic material upstream of anaerobic digestion, ii) stirring of the cellulosic material during anaerobic digestion, and/or and the disposal of unconverted feedstock solids from anaerobic digestion. With regard to the latter, the lignin in cellulosic biomass, which can make up 20% to 25% of the dry feedstock, is not generally digested during anaerobic digestion. The processes herein can produce fuel and/or product(s) from at least a portion of the undigested feedstock.

Of course, the above example and/or embodiments have been provided as examples only. It will be appreciated by those of ordinary skill in the art that various modifications, alternate configurations, and/or equivalents will be employed without departing from the scope of the invention. For example, although the digesters disclosed herein are particularly advantageous for converting agricultural residues and/or energy crops to biogas, in some embodiments the bales are co-digested with manure or another substrate (e.g., having a relatively high nitrogen content). In such co-digesting embodiments, it is preferable that most of the carbon in the feedstock comes from the baled material. For example, in one embodiment, less than about 20%, less than about 15%, or less than about 10% of the carbon in the feedstock will correspond to the manure. Accordingly, the scope of the invention is therefore intended to be limited solely by the scope of the appended claims.

The invention claimed is:

1. A process for converting cellulosic biomass to fuel, the process comprising:
- loading bales of cellulosic biomass into an enclosure;
- at least partially filling the enclosure with an aqueous liquid, wherein the aqueous liquid is filled to a level selected to at least partially submerge the bales of cellulosic biomass once loaded into the enclosure;
- providing anaerobic conditions within the enclosure containing the at least partially submerged bales;
- subjecting the bales loaded within the enclosure to an anaerobic digestion to produce biogas, the biogas comprising methane, the anaerobic digestion producing digestate; and,
- collecting at least a portion of the biogas produced from the anaerobic digestion of the bales of cellulosic biomass.

2. The process according to claim 1, wherein loading the bales of cellulosic biomass into the enclosure comprises stacking the bales within the enclosure.

3. The process according to claim 2, wherein the bales of cellulosic biomass have a density between 80 to 220 kg/$m^3$.

4. The process according to claim 1, comprising injecting water, an aqueous solution, inoculum, or any combination thereof, into a plurality of the bales of cellulosic material.

5. The process according to claim 1, wherein the enclosure is configured to hold at least about 25,000 $m^3$ of liquid.

6. The process according to claim 1, wherein the cellulosic biomass comprises agricultural residue.

7. The process according to claim 6, wherein the agricultural residue is straw.

8. The process according to claim 1, wherein the bales of cellulosic biomass have a nominal volume of at least 50 L.

9. The process according to claim 1, wherein the anaerobic digestion is a batch digestion, and wherein loading bales of cellulosic biomass into the enclosure comprises stacking the bales within the enclosure prior to at least partially filling the enclosure with the aqueous liquid.

10. The process according to claim 9, comprising removing the digestate from the enclosure after the biogas has been collected, said removing comprising driving a vehicle into the enclosure, the vehicle configured to transfer at least a portion of the digestate out of the enclosure.

11. The process according to claim 1, wherein the anaerobic digestion is a continuous digestion.

12. The process according to claim 1, comprising upgrading the collected biogas.

13. The process according to claim 1, wherein the collected biogas comprises carbon dioxide, and wherein the process comprises capturing at least a portion of the carbon dioxide and providing the captured carbon dioxide for storage.

14. The process according to claim 1, wherein providing anaerobic conditions within the enclosure comprises covering the bales of cellulosic biomass and the liquid with a flexible cover.

15. The process according to claim 1, wherein an average residence time of the bales of cellulosic biomass is greater than 30 days.

16. The process according to claim 1, comprising producing renewable natural gas from the collected biogas, wherein the fuel is at least one of the renewable natural gas, renewable hydrogen associated with the renewable gas, a fuel associated with the renewable gas, or a fuel associated with the renewable hydrogen.

17. The process according to claim 1, wherein the anaerobic digestion is conducted at a solids consistency not more than 15%.

18. A process for converting cellulosic biomass to fuel, the process comprising:
- loading straw bales into an enclosure, the loading comprising stacking the straw bales, each of the straw bales having a density between 80 to 250 kg/$m^3$;
- adding aqueous liquid to the enclosure such that the straw bales within the enclosure are in contact with the aqueous liquid, the aqueous liquid added to a level such that substantially all non-floating straw bales are submerged;
- introducing inoculum into at least one of the straw bales within the enclosure, the aqueous liquid, or the enclosure containing the submerged bales;
- sealing the enclosure containing the inoculum;
- subjecting the bales within the sealed enclosure to an anaerobic digestion to produce biogas, the anaerobic digestion conducted for at least 25 days; and,
- collecting at least a portion of the biogas produced from the anaerobic digestion of the straw bales.

* * * * *